(12) United States Patent
Rajendran et al.

(10) Patent No.: US 7,976,880 B2
(45) Date of Patent: *Jul. 12, 2011

(54) **PREGNANE GLYCOSIDE COMPOSITIONS AND *CARALLUMA* EXTRACT PRODUCTS AND USES THEREOF**

(76) Inventors: Ramaswamy Rajendran, Karnataka (IN); Kamala Rajendran, Karnataka (IN)

(*) Notice: Subject to any disclaimer, the term of this patent is extended or adjusted under 35 U.S.C. 154(b) by 72 days.

This patent is subject to a terminal disclaimer.

(21) Appl. No.: 11/114,185

(22) Filed: Apr. 26, 2005

(65) Prior Publication Data

US 2005/0202103 A1 Sep. 15, 2005

Related U.S. Application Data

(63) Continuation-in-part of application No. 10/837,613, filed on May 4, 2004, now Pat. No. 7,060,308.

(30) Foreign Application Priority Data

Jun. 4, 2003 (IN) .......................... 451/MAS/2003
Apr. 27, 2004 (IN) .......................... 384/CHE/2004

(51) Int. Cl.
 *A61K 33/04* (2006.01)
 *A61K 36/82* (2006.01)
 *A61K 36/54* (2006.01)
 *A61K 36/899* (2006.01)
 *A61K 36/48* (2006.01)
 *A61K 36/00* (2006.01)
 *A61K 31/16* (2006.01)

(52) U.S. Cl. ........ 424/728; 424/778; 424/757; 424/777; 424/750; 424/729; 424/739; 424/702; 514/627

(58) Field of Classification Search .................. None
See application file for complete search history.

(56) References Cited

U.S. PATENT DOCUMENTS

| 5,270,457 | A | 12/1993 | LaBella et al. | |
|---|---|---|---|---|
| 6,042,834 | A * | 3/2000 | Baraka | 424/745 |
| 6,376,657 | B1 | 4/2002 | Van Heerden et al. | |
| 6,703,051 | B1 | 3/2004 | Bates et al. | |
| 2001/0008638 | A1 * | 7/2001 | Wilding | 424/468 |
| 2003/0152648 | A1 * | 8/2003 | Corley et al. | 424/725 |

OTHER PUBLICATIONS

Hayashi et al., Phytochemistry, Four Pregnane Glycosides, Boucerosides AI, AII, BI and BII, from *Bourcerosia aucheriana*, 1988, vol. 27, pp. 3919-3924.*
Ahmad, Journal of Natural Products, New Pregane Glycosides from *Caralluma tuberculata*, 1988, vol. 51, pp. 1092-1097.*
Hibasami et al., International Journal of Molecular Medicine, 2003, vol. 11, pp. 23-26.*
Broca et al., 4-hydroxyisoleucine: experimental evidence of its insulinotropic and antidiabetic properties, 1999, Am J Physiol, 277: E617-E623.*
Venkatesh et al., Antihyperglycemic activity of *Caralluma attenuata*, prior art date Mar. 26, 2003, Fitoterapia, 74: 274-279.*
Bisdesmosidic Pregnane Glycosides from *Caralluma lasiantha*, Qui et al., Phytochemistry, vol. 50, Issue 3, pp. 485-491, Feb. 10, 1998.
S. Venkatesh, et al., "Antihyperglycemic activity of *Caralluma attenuata*", Fitoterapia, vol. 74, Issue 3, pp. 274-279 (2003).
Ramesh M, et al., "Antinociceptive and anti-inflammatory activity of carumbelloside-I isolated from *Caralluma umbellata*", Journal of Ethnopharmacol., vol. 68, Issue 1-3, pp. 349-352, Dec. 15, 1999.
M.N.M.Zakaria etal., "Evaluation of aintinociceptive and anti-inflammatory properties of *Caralluma arabica*", Pharm. Pharmacol., vol. 51 (Supplement), p. 117 (1999).
Ammar Bader, et al., "Further constituents from *Caralluma negenensis*", Phytochemistry 62 (2003) pp. 1277-1281.
Ahmed, M.M. et al., "Anti-inflammatory activity of *Caralluma tuberculata* alcholic extract," Nov. 20, 1992, Fitoterapia, vol. LXIV, No. 4, 1993.
Rizwani, G.H. et ail., "Biological Efficacy of the extracts and constituents of *Caralluma tuberculata* and *C. edulis*," J. Fac. Pharm. Gazi, 11(1), 43-53, (1994).
Zakaria, M.N.M. et al., "Anti-nociceptive and anti-inflammatory properties of *Caralluma arabica*," Journal of Ethnopharmacology, 76 (2001) pp. 155-158.
International Search Report from the WIPO issued in Applicant's corresponding International Patent Application No. PCT/IN2004/000150 dated Sep. 28, 2004.
K. Usmanghani, "Characterization of Chemical Constituents and Toxicity Evaluation of Some Poisonous Plants", 1992 Iowa State University Press, pp. 314-326 (XP009036963).
Viqar Uddin Ahmad et al., "New Pregnane Glycosides from *Caralluma tuberculata*", Journal of Natural Products, vol. 51, No. 6, pp. 1092-1097, Nov.-Dec. 1988.
Ghazala H. Rizwani et al., "Structures of Caratuberside E and F", Department of Pharmacognosy, Faculty of Pharmacy and HEJ Research Institute of Chemistry, University of Karachi, Pakistan, Apr. 14, 1994 (XP-001183719).
Ghazala H. Rizwani et al., "Caratuberside A2: A New Pregnane from *Caralluma tuberculata*", Spectroscopy Letters, 26(8), 1427-1434 (1993).
Alessandra Braca et al., "New pregnane glycosides from *Caralluma negevensis*", Tetrahedron 58 (2002) 5837-5848.
Sheng-Xiang Qiu et al, "Acylated C-21 Steroidal Bisdesmosidic Glycosides from *Caraluma umbellata*", Phytochemistry, vol. 46, No. 2, pp. 333-340, 1997.
Ahmed F. Halim etal., "Pregnane Glycosides from *Caralluma restrospiciens*", Phytochemistry, vol. 42, No. 4, pp. 1135-1139, 1996.
Mohammed Abdul-Aziz Al-Yahya et al., "Pregnane Glycosides from *Caralluma russeliana*", J. Nat. Prod. 2000, 63, 1451-1453.
Essam Abdel-Sattar et al, "Penicillosides A-C, C-15 oxypregnane glycosides from *Caralluma penicillata*", Phytochemistry 57 (2001) 1213-1217.

(Continued)

*Primary Examiner* — Michele Flood
*Assistant Examiner* — Catheryne Chen
(74) *Attorney, Agent, or Firm* — Robert E. Bushnell, Esq.

(57) ABSTRACT

Pregnane glycoside or a *Caralluma* extract including the pregnane glycoside of the present invention can be used for medical purposes and as food additives, such as a treatment of obesity, a reduction of blood glucose, a reduction of blood pressure, a reduction in hip, waist and arm circumferences, a reduction of fat, increase of BMR, a decrease of BMI, an increase of lean body mass, an appetite-suppression and a reduction/elimination of joint pain, anti-aging, a treatment for falling sex drive, the treatment for impotency and an erectile dysfunction, and an enhancement of energy levels.

40 Claims, 4 Drawing Sheets

OTHER PUBLICATIONS

Sheng-Xiang Qiu et al., "Bisdesmosidic pregnane glycosides from *Caralluma lasiantha*", Phytochemistry 50 (1999) 485-491.

Ki Young Lee et al., "New Acetylcholinesterase-Inhibitory Pregnane Glycosides of *Cynanchum atratum* Roots", Helvetica Chimica Acta—vol. 86 (2003) pp. 474-483.

Jeonghyung Lee et al., "Multidrug Resistance Reversing and Antiangigenic Activity of Pregnane Glycosides from *Cynanchum Wilfordii*", Korea Res Institute of Bioscience and Biotech, Taejon, SouthKorea, and Pusan National Univ. Pusan, South Korea (XP-001183726).

* cited by examiner

PREGNANE GLYCOSIDE COMPOSITIONS AND *CARALLUMA* EXTRACT PRODUCTS AND USES THEREOF

CROSS-REFERENCE TO RELATED APPLICATIONS

This application is a continuation-in-part application of U.S. patent application Ser. No. 10/837,613 filed on 4 May 2004 now U.S. Pat. No. 7,060,308. This continuation-in-part application makes reference to, incorporates the same herein, and claims all benefits including under 35 U.S.C. §120 from a co-pending application entitled *Caralluma* Extract Products and Processes for Making the Same filed in the United States Patent & Trademark Office on the 4 May 2004 and there duly assigned Ser. No. 10/837,613.

CLAIM OF PRIORITY

This application makes reference to, incorporates the same herein, and claims all benefits accruing under 35 U.S.C. §119 from an application for *CARALLUMA* EXTRACT PRODUCTS AND PROCESSES FOR MAKING THE SAME earlier filed in the Indian Patent Office on 4 Jun. 2003 and thereby duly assigned Serial No. 451/MAS/2003 and an application for TREATMENT AND MANAGEMENT OF OBESITY AND OBESITY RELATED DISORDERS/SYMPTOMS USING *CARALLUMA* EXTRACTS earlier filed in the Indian Patent Office on 27 Apr. 2004 and thereby duly assigned Serial No. 384/CHE/2004

BACKGROUND TO THE INVENTION

1. Field of the Invention

This invention relates to *Caralluma* extract, and, more particularly, this invention relates to a treatment and management of obesity and obesity-related symptoms/problems/disorders and other disorders using the *Caralluma* extracts, to pregnane glycoside compositions and method of making and using thereof.

2. Description of the Related Art

The *Caralluma* group of plants belongs to the Asclepiadaceae family and comprises a number of species that are distributed throughout the world. Some of these species include but are not limited to: *c. indica, c. fimbriata, c. attenuata, c. tuberculata, c. edulis, c. adscendens, c. stalagmifera, c. umbellata, c. penicillata, c. russeliana, c. retrospiciens, c. arabica and c. lasiantha*. Some of the species are distributed throughout various parts of India.

*Caralluma* plants are small, erect and fleshy. They have 4 grooved stems that are almost round in shape. They are generally devoid of leaves and form small flowers in a variety of dark colors. Their pods are erect, linear and about 2.5 cms in length and feel velvety to the touch. The thorns of *Caralluma* are soft. The species of *Caralluma* found in India are edible and form part of the traditional medicine system of the country.

The medicinal properties of *Caralluma* includes carminative, febrifugal, anthelmintic, anti-rheumatic, anti-diabetic and anti-hyperglycaemic, anti-pyretic, anti-inflammatory, anti-nociceptive, and anti-oxidant effects. The *Caralluma* extracts have been also found to be appetite-suppressants as well as CNS stimulants.

The medicinal properties of *Caralluma* have been attributed to the glycosides contained therein. A glycoside is a condensation product obtained from a sugar and non-sugar compound and may have further components such as ring structures that are substituted or non-substituted. The glycosides contained in *Caralluma* belong to the pregnane group of glycosides. Some of the pregnane group of glycosides found in *Caralluma* plants include, but are not limited to:

i. caratuberside A,
ii. caratuberside B,
iii. bouceroside I,
iv. bouceroside II,
v. bouceroside III,
vi. bouceroside IV,
vii. bouceroside V,
viii. bouceroside VI,
ix. bouceroside VII,
x. bouceroside VIII,
xi. bouceroside IX, and
xii. bouceroside X.

Another important property of *Caralluma glycosides* is their surprising synergy. This synergy was first observed by the present inventors. The synergy is exhibited by pairs of *Caralluma glycosides* and by higher order combinations, although the synergy contributed by the higher order combinations is not of much significance, in view of the fact that the content of glycosides other than the above-mentioned two, namely, caratuberside and bouceroside in *Caralluma* is extremely small. The caratuberside-bouceroside synergy is therefore, only one of the synergies found in *Caralluma glycosides*. The synergies found in *Caralluma glycosides* include the synergy arising out of isomer-isomer interactions in the two glycosides. The synergy is particularly strong with respect to the following three physiological effects of the glycosides: a reduction of body weight and treatment of obesity in subjects; a reduction of blood glucose in subjects and a reduction or elimination of arthritic and other joint pain. The uses of *Caralluma* for these physiological effects and the method of treatment thereof using *Caralluma* was first studied and investigated by the present inventors. The present inventors are also the first to study the related subject of the increase of muscle mass in subjects by use of *Caralluma* and the method of treatment for the same using *Caralluma*.

Obesity is a major public health problem. One of the major causes of obesity is the stressful and sedentary lifestyles of modern life and the widespread adoption of the diets that contain large amounts of high calorie processed foods. The problem is particularly acute and widespread in some industrialized countries.

Obesity is a direct causal contributor to a number of diseases and causes exacerbation in several others. Some of the disorders/symptoms include, but are not limited to diabetes, hypertension, cardio-vascular disease, atherosclerosis, and a stroke.

Obesity is being increasingly combated medically by the treatments and management for weight-reduction and for coping with, and management of the symptoms/disorders such as high blood sugar, blood pressure (b.p.), and joint pain.

Weight reduction and other related treatments such as regulation of BMI (Body Mass Index), an increase of lean mass, and an increase of BMR (Basal Metabolic Rate), are also being increasingly adopted by people who are not clinically obese but desire to feel and look good for personal or social reasons.

The known pharmaceutical options for treatment of obesity, that is, for weight reduction are a thermogenesis method, the lipase inhibitors, and the compounds that suppress appetite and/or stimulate the central nervous system (CNS).

The thermogenesis method involves the increase of the body core temperature slightly. This increases the metabolism of the deposited lipids in the body. Thermogenesis drugs act on the brain and the thyroid gland resulting in the increase of the body core temperature.

The lipase inhibitors work by reducing absorption of the fat in the intestine system. Thus, when a lipase inhibitor is administered to a subject, the fat portion of the food consumed by the subject passes through his intestinal system unabsorbed and is excreted into stools.

The appetite suppressants/CNS stimulators modify the levels of neurotransmitters such as catecholamine and serotonin in the blood, leading to a decreased feeling of hunger.

All three abovementioned approaches to the obesity treatment and management have been found to have unacceptable side effects.

The side effects associated with thermogenesis method include, by its nature, overstimulation of vital functions including cardiac rhythm, blood pressure, neurotransmitter levels and the endocrine system. The subjects under the thermogenesis method experience nervousness, anxiety, hypersensitivity to stimuli, insomnia and irregular heartbeats.

The side effects associated with the known lipase inhibitors are gastro intestinal (GI) in nature. The subjects under the lipase inhibitors treatment report oily and fatty stools and an increased bowel movement. They also complain of urgency of bowel movement and sometimes inability to control the same. Oily spotting may also occur between bowel movements. Another side effect is the loss of the fat soluble vitamins present in the food. They are carried away by the unabsorbed fat into the stools. For these reasons, patient compliance is found to be a problem in the lipase inhibitor treatments.

The side effects associated with the appetite suppressants and CNS stimulators include the altered neurotransmitter function. These include increased heart rate, hypertension, anxiety, mood alterations, diaphoresis, dizziness, swelling of extremities, dryness of mouth, constipation and insomnia.

The known obesity treatments are, furthermore, contraindicated in many clinical situations such as hypertensive obese patients or patients suffering from coronary artery disease, cardiomegaly and some chronic GI disorders such as Irritable Bowel Syndrome.

For the foregoing reasons, there is a need for a new treatment which has a minimal or transient side effect.

An interesting fact first observed by the present inventors is that the maximum caratuberside-bouceroside synergy is found when the caratuberside-bouceroside ratio is substantially equal to the CB ratio found in *c. indica*. Three other species, namely, *fimbriata, attenuata* and *tuberculata* have substantially the same ratio value and substantially the same glycoside content as *c. indica*. These four species are referred to hereinafter as Group I *Caralluma* species. Four more species, namely, *stalagmifera, umbellata, lasiantha* and *edulis* also have substantially the same CB ratio but somewhat lesser total content of glycosides than the Group I species. The latter four species are referred to hereinafter as Group II species and the caratuberside-bouceroside ratio is referred to as the CB ratio, or the CBR for short.

The prior art provides a process for extraction of *Caralluma* wherein the aerial parts of *Caralluma* plants are extracted by means of 10% aq. ethanol. The prior art process has a number of drawbacks and furthermore results in only a crude extract product that is not standardized, that is non-reproducible and that is not representative of the original plant material from which it is extracted. These drawbacks of the prior art product and process are described further hereinbelow.

In the first reference (M. N. M. Zakaria, M. W. Islam, R. Radhakrishnan, H. B. Chan, M. Kamil, A. N. Gifri, K. Chan, A. Al-Attas, J. of Ethnophamacology, 76 (2001), 155-158), *c. arabica*, a *Caralluma* species found in West Asia, was extracted using 10% aq. ethanol. The aerial parts of the plant were dried in the shade, powdered and then extracted with 10% aq. ethanol. The solvent was removed from the extract by evaporation under vacuum at 40° C. using a rotary evaporator. The dried extract was re-suspended in distilled water and the slurry used for a pharmacological investigation to establish the anti-nociceptive and anti-inflammatory properties of *c. arabica* with respect to mice and rats.

In the second reference (M. Kamil, A. F. Jayaraj, F. Ahmed, C. Gunasekhar, S. Samuel, K. Chan, M. Habibullah, J. Pham. Pharmacol. 1999, 5: (Supplement), 225), powdered *c. arabica* plant material was extracted using 10% aq. ethanol in a soxhlet extractor for eight hours. The flavone glycosides, luteolin-4'-O-nehesperidoside and kaempferol-7-O-nehesperidoside were isolated from the extract and the concentrations thereof in *c. Arabica* determined.

In the third reference (R. Radhakrishnan, M. N. M. Zakaria, M. W. Islam, X. M. Liu, K. Chan, M. Habibulah, J. Pham. Pharmacol., 1999, 5 (Supplement), 116.) and the fourth reference (M. N. M. Zakaria, M. W. Islam, R. Radhakrishnan, H. B. Chan, A. Ismail, K. Chan, M. Habibulah, J. Pharm. Pharmacol. 1999, 5 (Supplement), 117), the aerial parts of *c. arabica* are stated to have been extracted by means of 10% ethanol. No further details of the adopted process are disclosed.

The first drawback among the drawbacks of the prior art process is that decomposition of the *Caralluma glycosides* occurs during processing. This fact was not recognized by the prior art and was first observed by the present inventors. When a *Caralluma* extract (solution) is concentrated by evaporation of solvent therein, charring and overheating of material occurs at higher concentrations. The overheating/charring causes the decomposition despite the provision of considerable agitation.

The charring/overheating is primarily caused by the high viscosities of the *Caralluma* extracts of high concentrations. The high viscosities are caused by the presence of the resinous matter of *Caralluma* plants that get extracted out in the extract along with the glycosides. The present inventors observe that under certain conditions of extraction considerable quantities of the resins are extracted out along with the glycosides.

The decomposition was observed first by the present inventors both in the concentration step and in the extraction step. Where the extraction temperature is held at levels higher than 75° C., thermal decomposition of the glycosides occurs. Such high temperatures enhance the viscosity of the extract and increase the risk of decomposition in the concentration step.

In a soxhlet type apparatus, because of the column effect, the *Caralluma* plant matter would come into contact with solvent vapors that have a much greater ethanol content than 10% that is used to charge the apparatus. The extraction temperature would also remain generally above 75° C. Under these conditions, the present inventors have observed that considerable decomposition occurs and furthermore large quantities of the resinous matter in *Caralluma* plant matter get extracted out into the extract.

The process conditions are not fully disclosed in the third and fourth references but it is fair to assume that the extracts are evaporated to dryness to obtain the product in a solid form suitable for pharmacological studies. Thus, the decomposition must certainly occur in the method adopted by the third and fourth references.

The second drawback of the prior art process is that the non-glycoside components in *Caralluma* are extracted. The non-glycoside components are tannins, pectins and the resinous matter and others. The present inventors have found that at low ethanol concentrations considerable quantities of tannins and pectins are extracted out with the glycosides while at high concentrations the resins go preferentially into solution. These inventors observe that, when 10% aq. ethanol is used, an extract contains considerable percentage of the tannins and pectins. So, in the process conditions adopted in the first, third and fourth references, the *Caralluma* extract obtained would have considerable impurities in the form of tannins and pectins that have a deleterious effect on the shelf life of the glycoside product. In the second reference, ethanol concentrations of over 80% are likely to be encountered by the *Caralluma* plant matter in the soxhlet apparatus. The present inventors have found that the extract under these conditions would contain high amounts of the *Caralluma* resins.

The third drawback of prior art is that the *Caralluma* extract product obtained by the prior art process is non-standard in so far as the composition thereof would vary from one extraction to another. It is unrepresentative in so far as it would not reflect fully either the various constituents of *Caralluma glycosides* or their relative proportions that are found in the original plant matter. Further, as the composition would vary from extract to extract the *Caralluma* extract product of the prior art process cannot be considered to be reproducible.

Apart from the pharmacological studies of a few of the medicinal aspects of *Caralluma*, the prior art does not provide for any concrete medical applications of *Caralluma*. The present inventors have pioneered such applications. The applications would require *Caralluma* constituents in various forms such as tablets, injectables and others which would have to be made from a suitable intermediate that contains the principles of *Caralluma*. Such an intermediate that contains the principles of *Caralluma* and that could be the starting point is neither known or defined in the prior art.

In summary, the drawbacks of the prior art process include, but are not limited to:
  i. non-standardized, non-representative and non-reproducible product;
  ii. process conditions conducive to the decomposition of the glycosides;
  iii. the extraction of undesirable non-glycoside components of *Caralluma* into the extracts, such as the tannins, pectins and resins that would affect the purity and storage properties of the product and that have side effects on the subjects treated with *Caralluma glycoside* products;
  iv. no provision for removal of the undesirable non-glycoside components from the extracts in the process of prior art; and
  v. process parameters not optimized from the point of view of process economics or from the point of view of obtaining the desirable *Caralluma* intermediate product(s).

SUMMARY OF THE INVENTION

It is therefore an object of the present invention to provide a treatment and management method of obesity, overweight, high BMI(Body Mass Index), low BMR(Basal Metabolic Rate), hypertension, hyperglycaemia, hypercholesterolemia, osteo-arthritis, migraine, clinical depression, loss of hearing, a sexual dysfunction, low stamina, endurance and energy levels, reduced cognitive and memory functions, capillary degeneration, joint inflammation/degeneration, circulation disorder, aging syndrome, menopausal syndrome and others; in the alteration/improvement/regulation of conditions/parameters/functions such as appetite level, weight, BMI, BMR, waist, arm and hip circumferences, fat levels, lean body mass, blood sugar, blood pressure(bp), total blood cholesterol, blood HDL/LDL ratio, stamina, energy and endurance levels, cognitive and memory function, hearing, aging, joint mobility, mood, sexual stamina and power, capillary health and others and in skin nourishment and as an anti-oxidant, anti-inflammation and anti-depressant agent.

It is also an object of the present invention to provide methods of the above treatment/management and of the alteration/improvement/regulation and to pregnane glycoside compositions therefor, the compositions optionally further comprising additional therapeutical, nutraceutical or nutrition components.

It is also another object of the present invention to provide processes for admixture for making the compositions.

It is still an object of the present invention to provide methods of treatment and management of obesity and the obesity related symptoms/disorders and for the alteration/improvement/regulation by the administration of effective doses of the pregnane glycoside(s) or the mixtures or the extracts.

It is further an object of the present invention to provide pregnane glycoside compositions for the uses and methods.

It is yet another object of the present invention to provide processes for making the compositions by the admixture of the constituents thereof.

In order to achieve the above and other objectives,

BRIEF DESCRIPTION OF THE DRAWINGS

A more complete appreciation of the invention, and may of the attendant advantages, thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
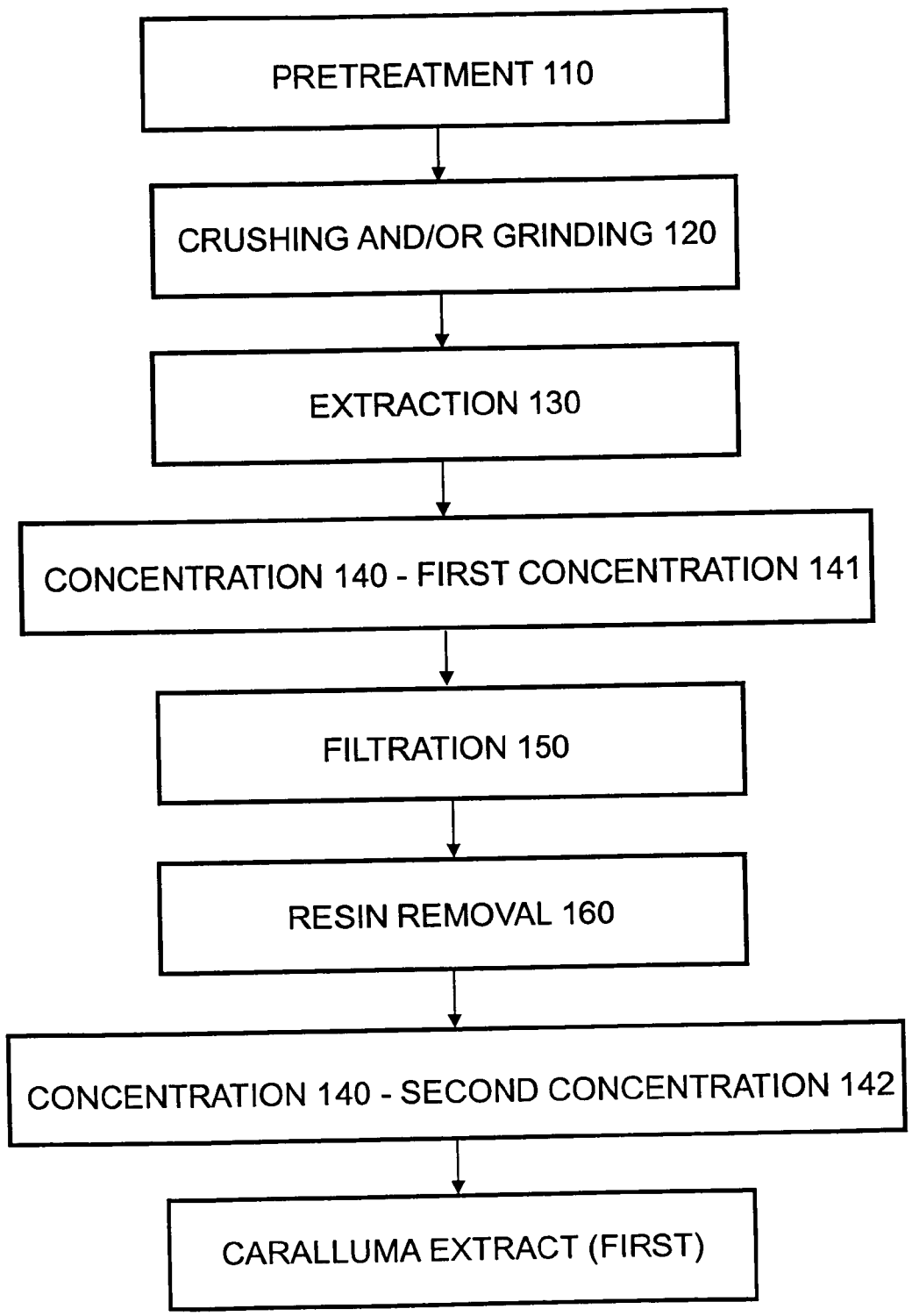
FIG. 1 shows an example of the process for making the first *Caralluma* extract from *Caralluma* plant matter.

In this specification, depending on the context the term 'extraction' refers either to the process of extraction as a whole or to the individual step of extraction (leaching) that forms a part of the process. In the individual step of extraction, *Caralluma* plants, or parts thereof, are contacted with a suitable solvent that extracts out (leaches out) one or more constituents/components thereof. Similarly, the term 'extract' refers, depending on the context, either to the solution that is obtained during, and/or at the end of the extraction step, or to the solid mass that would be obtained upon removal by evaporation or otherwise, of the solvent contained in the solution. The solid mass is also sometimes referred to herein as the 'solute', which has also been used herein to refer to the one or more components of *Caralluma* that are soluble in the solvent. The soluble components may be desired ones from the point of view of extraction or otherwise.

In this specification, the term "solvent" includes solvent mixtures unless the context requires otherwise, that is, the expression 'solvent/solvent mixture' has been shortened to 'solvent' in the interests of clarity and conciseness.

In this specification, the terms '*Caralluma* plant material' or 'plant material' or 'plant matter' refer to the raw material at the commencement of the process, the 'plant material' at various stages of processing in the processes of the invention being referred to as 'material-in-process'. However, for the sake of clarity and conciseness the term 'plant material' or 'plant matter' is also used to refer to the 'material-in-process' at various stages of the process.

The "first *Caralluma* extract" product (or the *Caralluma* extract, Technical) refers to a product that is designed to be a suitable starting material, intermediate, for a number of pharmaceutical products containing the principles of *Caralluma*, or a liquid product. The first *Caralluma* extract may contain one or more or all the glycosides of *Caralluma*. Similarly, the proportions of the glycosides therein may have any set of values. Preferably, the product contains at least both the major pregnane glycosides of *Caralluma*, namely, caratuberside and bouceroside. Further, it is preferred that the proportion of the two major glycosides is substantially the same as the proportions found in the *Caralluma* species of the Groups I and II. That is, the CBR, the ratio of caratuberside and bouceroside therein is preferably 9:1 to 11:1. Further, it is also preferred that the resin content in the first *Caralluma* extract product does not exceed 0.5% by wt.

The second *Caralluma* extract (or the Standardized *Caralluma* extract) of the invention refers to a product that is further processed from the first *Caralluma* extract. The second *Caralluma* extract is designed to be a suitable starting material (intermediate) for several pharmaceutical products containing the principles of *Caralluma*. The second *Caralluma* extract contains the glycosides of *Caralluma* and may contain one, more or all of the glycosides within the scope of the invention. Similarly, the glycosides may be in any relative proportion. Preferably, the extract contains both the pregnane *Caralluma glycosides*, namely, caratuberside and bouceroside and preferably they are substantially in the proportions as found in *Caralluma* species of the Group I and II, that is, a CBR of 9:1 to 11:1. Preferably the resin content in the second *Caralluma* extract does not exceed 1.0% by wt.

The present invention and, particularly, the term "*Caralluma* extract" or "*Caralluma* plant material" means that the extract or the material is from any species of *Caralluma* group even if this specification does not list all the species of *Caralluma* group.

Typical compositions of the first *Caralluma* extract product of the invention of the two preferred concentrations are given below.

TABLE 1

The first *Caralluma* extract (from Group I Species)

| Test parameter | Specification |
| --- | --- |
| Appearance | brown to dark brown liquid |
| Solubility in water | soluble |
| Total dissolved solids | 65% minimum w/w |
| Total Bitters | 1.5% minimum w/w |
| Total Saponin glycoside | 5% minimum w/w |
| Total pregnane glycosides | Above 15% w/w |
| Resinous matter | not more than 0.5% w/w |
| Total microbial count | 5,000 cfu/gm. maximum |
| *E. coli* and *salmonella* | absent |
| Coliforms | absent |

TABLE 1-continued

The first *Caralluma* extract (from Group I Species)

| Test parameter | Specification |
| --- | --- |
| *P. aeruginosa* | absent |
| *S. aureus* | absent |
| Heavy metals | 10 ppm maximum |

TABLE 2

The first *Caralluma* extract (from Group II Species)

| Test parameter | Specification |
| --- | --- |
| Appearance | brown to dark brown liquid |
| Solubility in water | soluble |
| Total dissolved solids | 65% minimum w/w |
| Total Bitters | 0.5% minimum w/w |
| Total Saponin glycoside | 2% minimum w/w |
| Total pregnane glycosides | 5%-15% w/w |
| Resinous matter | not more than 0.5% w/w |
| Total microbial count | 5,000 cfu/gm. maximum |
| *E. coli* and *salmonella* | absent |
| Coliforms | absent |
| *P. aeruginosa* | absent |
| *S. aureus* | absent |
| Heavy metals | 10 ppm maximum, , |

The processes according to the present invention can provide any desired concentration of the glycosides in the products by suitable operation of the extraction and concentration steps and of the other steps. The two preferred concentration ranges of the first *Caralluma* extract are by way of example, that is, by way of preferred embodiments and should not limit the scope of the invention.

It is preferred to make the *Caralluma* extract containing substantially all the glycosides of *Caralluma*, the desired CBR, low non-glycoside components such as tannins, pectins and resinous matter.

The glycoside content of the second *Caralluma* extract may have any value according to the present invention. After considering the process economics including the costs of extraction, and the desirable specification of the Extract for downstream processes, and the glycoside contents of the Group I and II species, the present invention has arrived at two preferred concentrations of the second embodiment of the *Caralluma* extract, namely, a pregnane glycoside content of over 30% and from 25% to 30%. The two glycoside contents are the specifications obtained by extracting the Group I and II species, respectively, using the processes of the inventions in a generally optimized manner.

The second *Caralluma* extract of the invention preferably comprises the *Caralluma glycosides* adsorbed on an excipient and is in the powder form. The preferred composition of The second *Caralluma* extract is given in Tables 3 and 4.

TABLE 3

The second *Caralluma* extract (from Group I *Caralluma* species)

| Test parameter | Specification |
| --- | --- |
| Appearance | brown to dark brown powder |
| Solubility in water | 75% minimum w/w |
| Loss on drying | 10% maximum w/w |
| Total Bitters | 3% minimum w/w |
| Total saponin glycoside | 10% to 30% w/w |

TABLE 3-continued

The second *Caralluma* extract
(from Group I *Caralluma* species)

| Test parameter | Specification |
| --- | --- |
| Total pregnane glycosides | above 30% w/w |
| Resinous matters | Not more than 1% w/w |
| Total microbial count | 5,000 cfu/gram maximum |
| E. coli and salmonella | absent |
| Coliforms | absent |
| P. aeruginosa | absent |
| S. aureus | absent |
| Heavy metals | 10 ppm maximum |

TABLE 4

The second *Caralluma* extract
(from Group II *Caralluma* species)

| Test parameter | Specification |
| --- | --- |
| Appearance | brown to dark brown powder |
| Solubility in water | 75% maximum w/w |
| Loss on drying | 10% maximum w/w |
| Total bitters | 1% minimum w/w |
| Total saponin glycoside | 3% to 5% w/w |
| Total pregnane glycosides | 25%-30% w/w |
| Resinous matters | not more than 1% w/w |
| Total microbial count | 5,000 cfu/gm. maximum |
| E. coli and salmonella | absent |
| Coliforms | absent |
| P. aeruginosa | absent |
| S. aureus | absent |
| Heavy metals | 10 ppm. Maximum |

The purpose of the excipient is to adsorb the *Caralluma glycosides* thereon and further to provide an extended surface area for rapid and substantially complete removal of the traces of water, the extraction solvent and the resin dissolving solvent if used. Any of the known excipients can be used. The preferred excipients are maltodextrin and magnesium carbonate.

Figure 2:
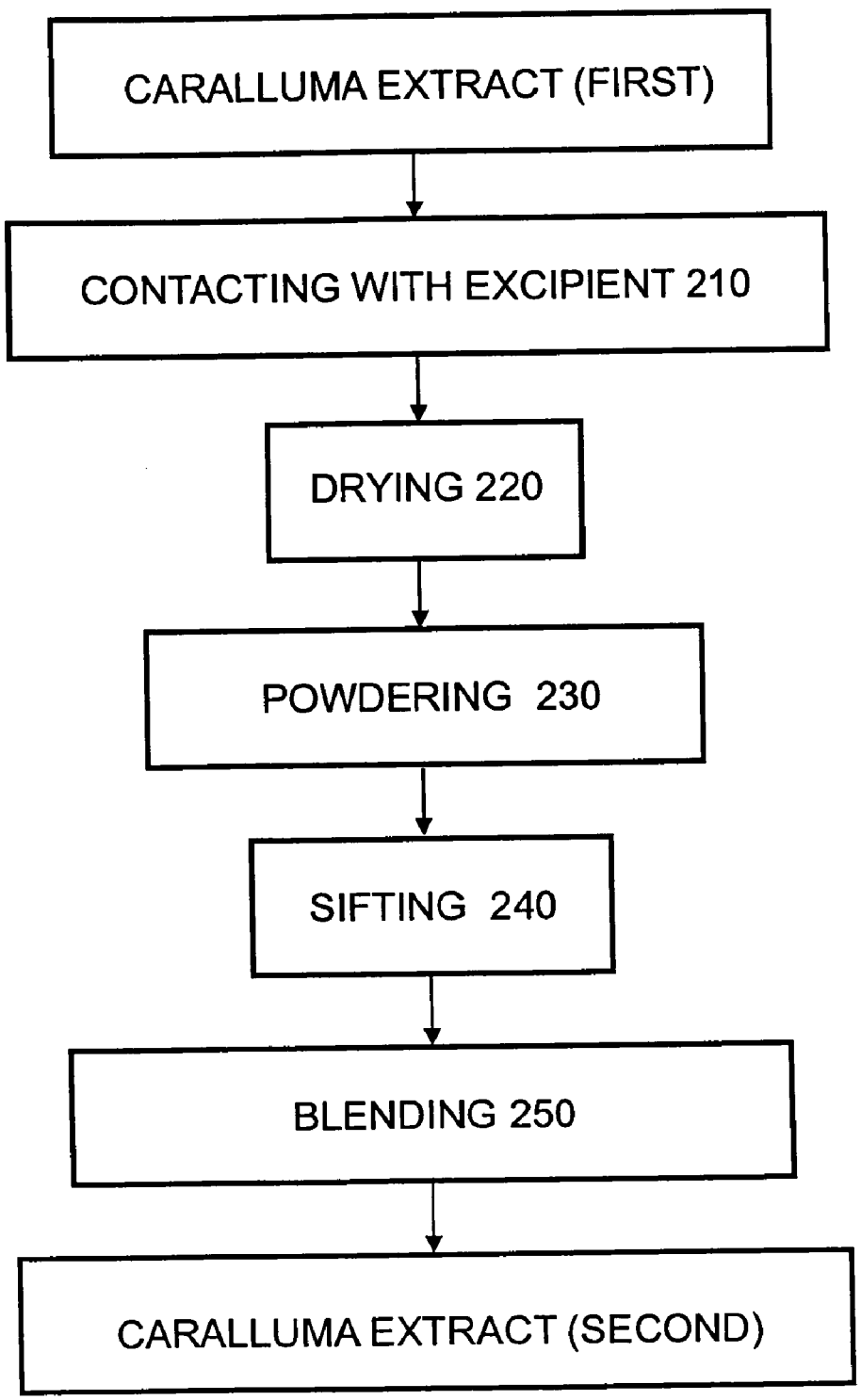
FIG. 2 shows an example of the process for making the second *Caralluma* extract from the first *Caralluma* extract.
Figure 3:
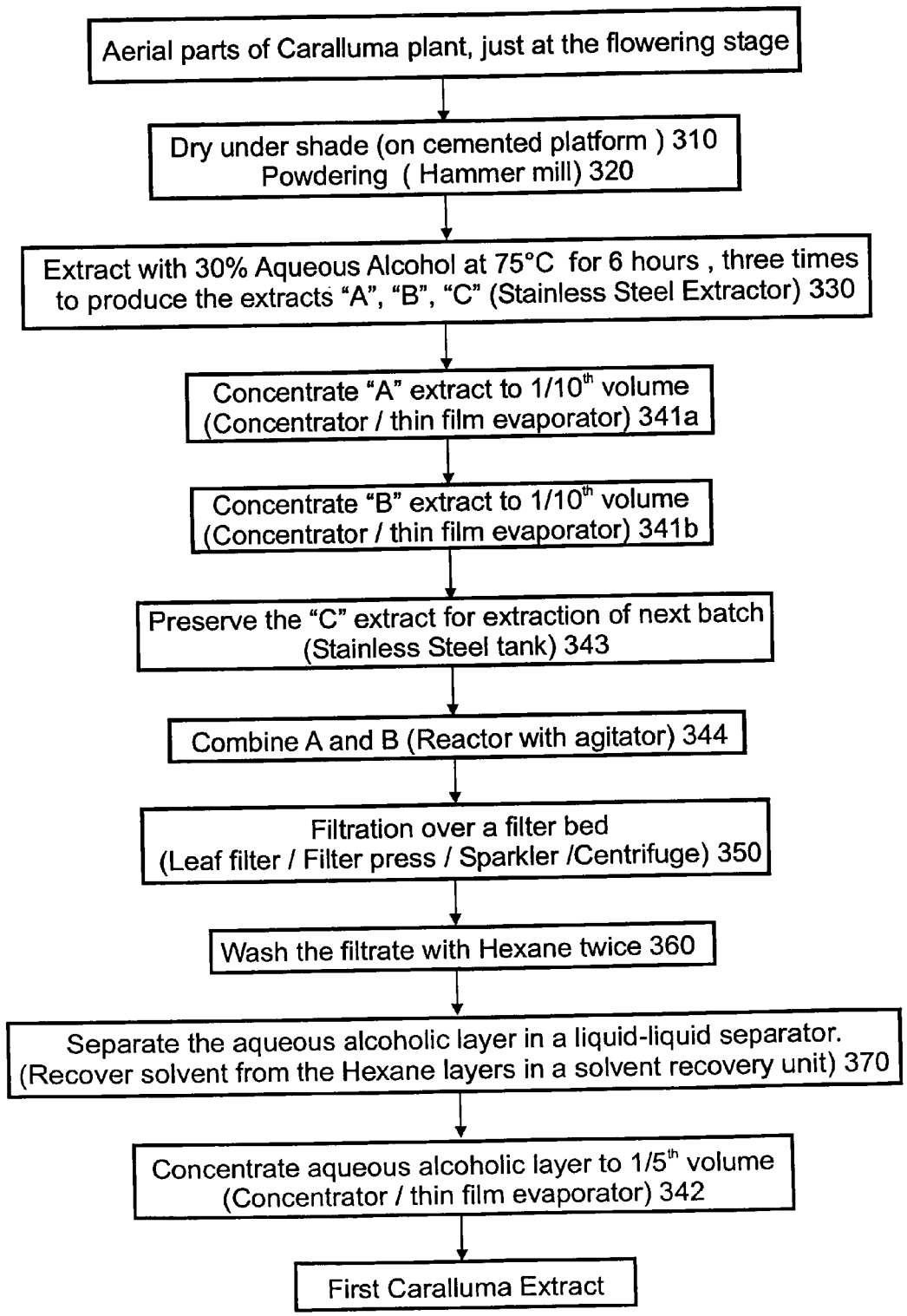
FIG. 3 shows one of the preferred processes for making the first *Caralluma* extract from *Caralluma* plant matter.
Figure 4:
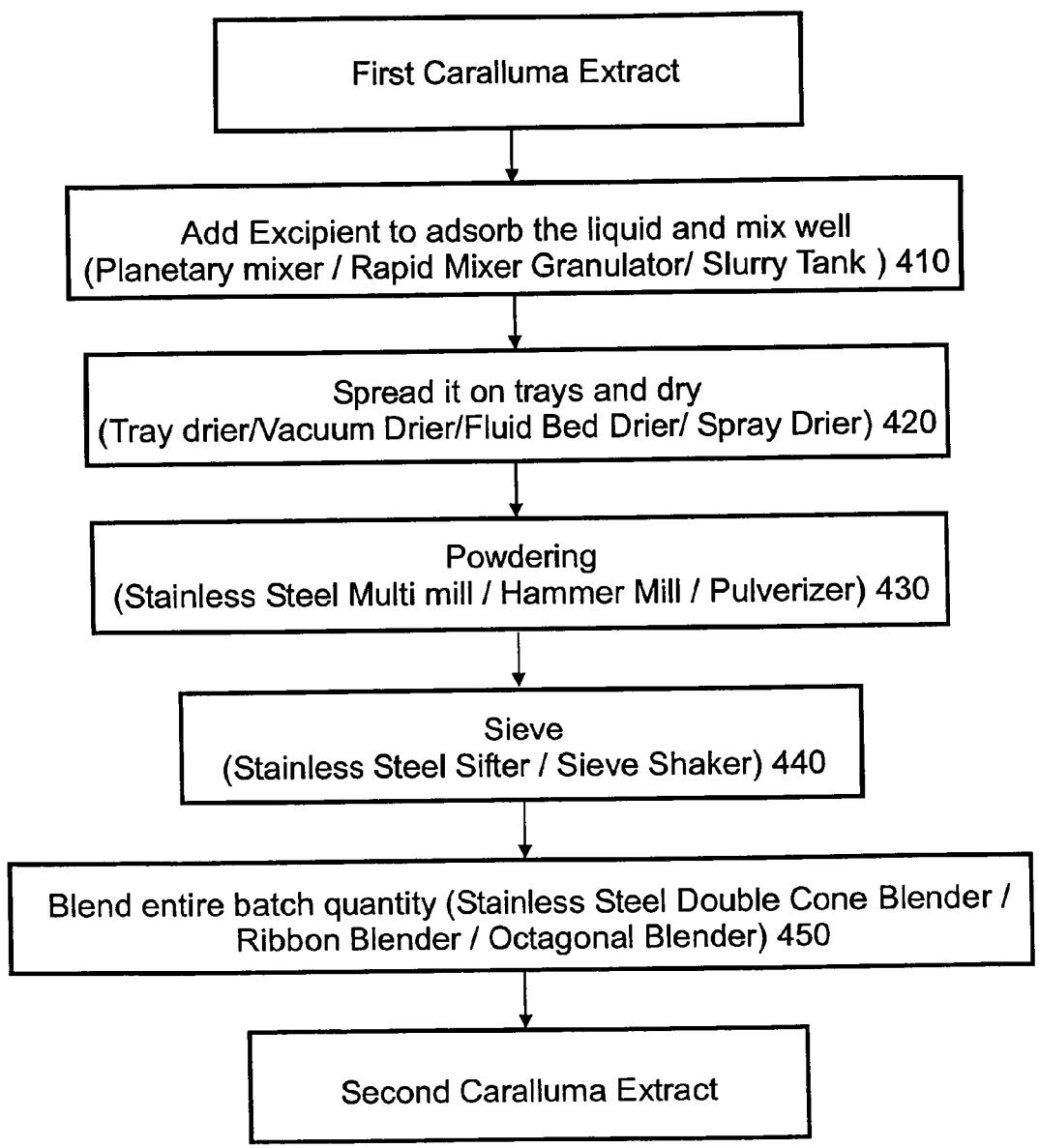
FIG. 4 shows one of the preferred processes for making the second *Caralluma* extract from the first *Caralluma* extract.

FIG. 1 shows an example of the process for making the first *Caralluma* extract from *Caralluma* plant matter. FIG. 2 shows an example of the process for making the second *Caralluma* extract from the first *Caralluma* extract. FIG. 3 shows one of the preferred processes for making the first *Caralluma* extract from *Caralluma* plant matter. FIG. 4 shows one of the preferred processes for making the second *Caralluma* extract from the first *Caralluma* extract.

The first step 110 comprises one or more optional pretreatment operations such as washing, cleaning, soaking, drying, cutting, chopping, blanching, and others, if necessary.

The plant material is preferably extracted as a powder. Thus, if the plant material is in large pieces, a cutting/chopping operation would be desirable to reduce it to a smaller size so that it can be ground to the desired mesh size for the extraction operation. Reducing the plant material size provides better contact during extraction and consequently faster extraction and also better heat transfer and uniformity of bed temperature in the extractor. Very fine plant material may tend to form lumps during extraction reducing the solid-liquid contact.

The crushing and/or grinding 120 of the raw plant material or the plant material obtained from the pretreatment are also optional. In this application, the term "crushing" includes crushing or grinding, or both. A number of grinding apparatus/equipments are available and are within the scope of the invention. A swing hammer mill is preferably used. If the plant material is in pieces rather than a powder, larger equipment is required for the same batch size, and a larger amount of solvent (or mixture) would also be necessary per batch. The batch times would also be correspondingly higher. The preferred size of the material-in-process after grinding is −10 BSS to +80 BSS. The extraction step 130 may be carried out by any of the several known methods such as batch, continuous, counter-current, series arrangement, parallel arrangement and others, by combinations of one or more of these, by hybrid schemes formed by fusing one or more of the methods.

One preferred example of the extraction method is of semi-parallel batch extraction with semi-countercurrent solvent feed. For instance, where a batch of plant material undergoes three separate extraction operations, a plurality of extractors are used. The three operations are referred to herein as "E1", "E2" and "E3". The solvent feed in the operation "E1" is not pure solvent but the somewhat weak extract obtained from the operation E3 of extraction. The solvent feed charged in the operations "E2" and "E3" is substantially pure solvent, which may be either fresh solvent or recovered solvent. The "A", "B" and "C" refer to the extracts(solutions) obtained in the operations, E1, E2 and E3, respectively. In the extraction step 130, undesirable non-glycoside components of *Caralluma* are also extracted, such as the tannins, pectins and resins that would affect the purity and storage properties of the product and that have side effects on the subjects treated with *Caralluma glycoside* products or *Caralluma* extracts.

Numerous combinations of the extraction methods, extraction schemes and solvent feed systems are possible. The choice of the extraction method may be governed by process economics factors such as solvent costs and availability, solvent recovery costs, batch times, energy costs for the heating of extractor contents, capital costs of various types of extraction equipment and others. Such factors vary from region to region and location to location. A wide range of extraction equipment is available. The choice is usually made on cost considerations and with the idea of keeping the batch times to the minimum. One preferred example of the extractor equipment is a jacketed stainless steel extractor.

The selection of the solvent is important. In view of the problems recognized by the inventors, a solvent should offer a good rate of extraction at low temperature and possess low solubility for the resins and also for the tannins and pectins. The rate of solubility of resins, tannins and pectins should also be as low as possible at the conditions adopted for extraction. That is, it is important to optimize a solvent and conditions of extraction (e.g., temperature and duration of extraction) so that the dissolution of the resinous matter is so reduced as to eliminate the necessity of the optional resin removal step and the entire concentration can be carried out in the first stage of concentration.

The present inventors have investigated a number of solvents for the extraction such as acetone, isopropyl alcohol, ethylene dichloride, n-hexane, n-butanol, water, methanol, ethanol, aq. methanol and aq. ethanol in view of the above factors.

100% methanol gives a poor yield of glycosides and extracts a large amount of resinous matter. This pushes up the solvent costs and solvent recovery costs of resin extraction. Similar results are obtained with methanol of 40% to 100% strength. The best yield of glycosides with a particular batch time is found to be with 20%-40% methanol. But the resin extraction is still high. Because of the resin extraction, the product gets sticky and hygroscopic. Accordingly, a resin removal operation is preferably performed. For example, when methanol is used as a solvent for extraction, n-hexane can be used for resin removal.

Use of ethylene dichloride as solvent without resin removal gives a sticky and hygroscopic *Caralluma* extract product. If resin removing solvent such as high strength aq. ethanol is used, the product is better but the yield of glycosides with ethylene dichloride is low compared to the use of 30% aq. ethanol where other parameters are substantially the same. The solvent costs and solvent recovery costs are high for both the extracting solvent and for the resin dissolving solvent.

Use of isopropyl alcohol as solvent gave a good yield of glycosides. n-Hexane was used as the resin removing solvent. When isopropyl alcohol was used, the *Caralluma* extract product was found to be of acceptable quality. However, isopropyl alcohol is a costly solvent.

If water is used as a solvent with the resin dissolving solvent of n-butanol, the yield as well as the product quality is poor. In addition, n-butanol is an expensive solvent.

Costwise, ethanol is preferable to other solvents. Aqueous ethanol may give a good yield of glycosides. It is observed that, at higher strengths, the aqueous ethanol tends to extract more resin than at lower strengths, and that, at lower strengths, it tends to pick up more of the tannins and pectins than at higher strengths. Accordingly, the optimization of the concentration is important. It is preferred that the ethanol is of 10%-85% strength. It is also preferred that the ethanol concentration is 20%-40% by volume to get a good yield of glycosides.

Various solvent mixtures were investigated by these inventors such as mixtures of n-butanol, ethyl acetate and ethylene dichloride with ethanol, methanol, aq. ethanol, aq. methanol and others. The yields and the product quality were good. The cost was the constraint as n-butanol, ethylene dichloride and ethyl acetate are expensive solvents.

While the extraction at the higher temperature tends to keep the batch times shorter, the decomposition of glycosides increases with temperature. Therefore, the optimization of the temperature should be considered. Preferably, the extraction should be done in the temperature range of 70-80° C. when using aq. ethanol as solvent. More preferably, the extraction should be done in the temperature range of 70-75° C. because, where the extraction temperature is held at levels higher than 75° C., thermal decomposition of the glycosides occurs. Such high temperatures enhance the viscosity of the extract and increase the risk of decomposition in the concentration step.

Batch times can be controlled by controlling the temperature of extraction and the scheme of extraction adopted, solvent used, degree of agitation and others. With 20-40% aq. ethanol as solvent and extraction at 70-80° C. preferably the extraction is carried out in 3-4 stages, of which each batch time is about 5-8 hours. In these stages, either fresh solvent or weak solution(s) from other extractions is used.

The step 140 is a concentration step. Numerous methods of desolventification (solvent removal) including evaporation are available. It will be apparent to those skilled in the art that numerous methods for the concentration step 140 will also serve effectively.

The evaporated solvent may be recovered if desired.

The temperature of the evaporation is important. Where aq. ethanol is used, the evaporation is more preferably carried out at temperatures from 40° C. to 50° C. under vacuum.

A plurality of extract batches may come out from the extraction step 130. In the first stage of the concentration step 141, the concentration of the extract batch(es) may be carried out in a single operation or in a plurality of operations. Still further, where the plurality of batch(es) are present, the concentration operation may be carried out singly on each batch or on mixtures of one or more of the batches. Such combinations offer plant operational flexibility and scope for optimizing usage of plant.

For example, where the extract batches "A" and "B" come out from the extraction step 130, the extract batches "A" and "B" may undergo a first concentration operation singly to about one-tenth of the original volumes thereof. Subsequently, the batches "A" and "B" may be mixed and then concentrated further to about one fifth of the starting volume thereof. The concentration of the pregnane glycosides at the end of the mixed batch is preferably about 3-8% by wt. The preferred concentration is below the range at which any significant decomposition occurs.

The viscosity of an extract being concentrated goes up with increasing glycoside concentration. This problem is further compounded by the presence of the resinous matter in the extract. In fact, where glycoside concentration is above 3-8% by wt., overheating and/or charring may occur due to the high viscosity. Therefore, if the extract contains a large amount of resinous matter, it is advisable to terminate the first stage of concentration at this point and undertake the resin removal step 160 as it is the resin that is responsible for the high viscosities. After the resin removal, further concentration (i.e., the second stage of concentration 142) may be taken up. The first and second concentration stages 141, 142 may comprise a plurality of individual concentration operations. Accordingly, it is preferred that the resin removal step 160, if required, be carried out after the first stage of concentration 141 and before the second stage of concentration 142. The reduced volume of the partially concentrated solution(s) can reduce the requirement of the resin dissolving solvent.

The partially concentrated solution(s) at the end of the first concentration step 141 may include particulate impurities. An optional filtration operation 150 may be taken up at this stage to remove the particle impurities before sending the solution(s) to the second stage of concentration 142, or to the optional resin removal step 160 or before returning one or more solution(s) to the extractor(s) to reuse the solvent for the solvent feed for extraction step 130.

Whether or not the resin extraction is exercised depends on the resin content of the original plant material and how much the resin is extracted into the extract (i.e., solution). The latter depends on the nature of solvent and its concentration, and the conditions of extraction such as temperature and duration, agitation and others.

The resin removal 160 may be done as part of the pretreatment step 110. n-Hexane can be used as the resin dissolving solvent. Where substantially complete resin removal is achieved, the concentration step 140 can be done in one stage because the entire concentration even up to substantial total dryness could then be done in the first stage 141 without any noticeable decomposition. The resin removal 160 with n-hexane may be done with or without refluxing of the solvent. The drawback in this embodiment is that the consumption of n-hexane which is expensive is high.

The resin removal step 160 can also be done between the pretreatment step 110 and the crushing/grinding step 120. After the pretreatment step 110, the plant material is generally of a reduced size so that the requirement of the resin dissolving solvent is reduced.

The resin removal step 160 can be carried out after the crushing/grinding step 120. In this arrangement, there would be further reduction in the amount of solvent required because the crushing/grinding step 120 makes the material to be contacted with the solvent still finer. This has the effect of reducing the batch times for resin extraction.

The resin removal step 160 may be carried out also after the extraction step 130. If done at this stage, it would therefore be a liquid-liquid extraction operation. Contacting two liquids is a far more efficient operation and consequently the required amount of the solvent would be still less at this stage when all other conditions are equal. The number of batch times is also reduced.

Even if it is preferred that the resin removal step be carried out after the first stage of concentration 141 and before the second stage of concentration 142, different decisions as to when the resin removal step is carried out can be made on the basis of the cost and the availability of the resin solvent.

A number of resin dissolving solvents were tried in this invention, such as n-hexane, petroleum ether, benzene, toluene, diethyl ether, methylene dichloride and ethylene dichloride. The resin dissolving solvent can be selected on the basis of the cost of the process and on the cost and availability of the solvent and on considerations such as toxicity, ease of trace removal and others. In the present invention, n-hexane is preferred.

Generally speaking, if the resin content is desired to be reduced to the preferred values of not more than 0.5% w/w for the first *Caralluma* extract product and not more than 1.0% by wt for the second *Caralluma* extract product, it would be necessary to carry out the resin removal step 160. However, as mentioned hereinabove, this depends on the original resin content in the plant material and how much of it comes out in the extracts (solutions) during the extraction step.

The resin removal step 160 may include the step of washing the optionally filtered first concentrate, (the solution(s) obtained after the first concentration stage 141) with a suitable solvent that can dissolve the resinous matter contained in the filtrate. The washing (or leaching) may be carried our one or more times. The washing step is preferably a liquid-liquid extraction process and any of the various equipment known in the art for the purpose may be used.

The washed filtrate is subjected to a separation operation that results in two layers, one of which is a heavy layer having the glycosides in solution and the other of which is a light layer having the resin dissolving solvent. The separation can be carried out in any of the known equipment/apparatus available in the art for the purpose and adoption of any of them is within the scope of the invention.

The light layer having the resinous matter in solution is either discarded or subjected to a solvent recovery operation by any of the known means of solvent removal provided in the art. Preferably the solvent recovery is done by evaporation and condensation of the solvent.

The heavy layer contains the *Caralluma glycosides* and is subjected to the second concentration stage 142. Like the first concentration stage 141, the conventional concentration steps and their variations will be apparent to those skilled in the art. Preferably, the concentration 140 is done by evaporation of the solvent under vacuum using thin film evaporators.

The preferred temperature range for the evaporation is 40 to 50° C. when aq. ethanol is used as the extracting solvent. The evaporated solvent can be recovered by condensation. The selection of the method of solvent removal and of the equipment therefor is to a large extent based on cost factors.

The concentration is continued until the desired concentration of glycosides is reached. The heavy layer, that is, the concentrated solution at this stage constitutes the first *Caralluma* extract product of the invention.

As shown in FIG. 2, the second *Caralluma* extract product can be made from the first *Caralluma* extract.

The first *Caralluma* extract is first contacted with a suitable excipient 210. The contact may be carried out in any of the mixing apparatus/equipment such as, for example, planetary mixers, rapid mixers, granulators, slurry tanks and others that are found in the art. A number of suitable excipients are available in the art and may be used in the process of the invention. The preferred excipients are maltodextrin and magnesium carbonate.

Along with the excipient, the binders (binding agents) may be added if required or desired. Any of the known binding agents may be used in the process of the invention. Preferably, the binder is selected from the following, starch, gum Acacia, guar gum and polyvinyl pyrolidone. The mixing is continued until the adsorption of the first *Caralluma* extract on the excipient particles is completed, and the particles have a homogeneous coating of the glycosides and the binder, if used.

At this stage the material-in-process is removed and subjected to the drying step 220. The drying 220 is carried out by any of several methods of drying and by any of the many drying apparatus/equipment that are available in the art. Tray driers, fluid bed dryers, spray driers and vacuum driers are some of the drying apparatus/equipment available in the art. A tray drier and a spay dryer are preferred. The spray-drying makes the product sticky and hygroscopic. For example, the blended material from the excipient step 110 may be thinly spread on the trays of the tray drier. This assists and accelerates the evaporation of the final traces of moisture, extraction solvent and the resin dissolving solvent. Accordingly, the excipient may be used for performing both an adsorption function and a function of facilitating further drying.

The dried material is basically the second *Caralluma* extract of the invention. Preferably, it is subjected to a grinding/milling (powdering) operation 230 to obtain a fine powder. The conventional equipment/apparatus such as multi-millers, hammer mills and pulverizers can be used for the grinding/milling step 230.

The product from the grinding/milling step 230 is then sifted in any of the known sifting, equipment/apparatus such as, but not limited to, a sieve shaker or sifter 240.

The sifted material is then blended in a blending machine such as, but not limited to, double cone blender, a ribbon blender, or an octagonal blender 250.

The output from the blending step 250 is the second *Caralluma* extract of the invention in a powder form.

In order to provide a clearer understanding of the invention and without limitation to the scope thereof, some examples will now be described and illustrated in FIGS. 3 and 4.

Example 1

The aerial parts of *Caralluma fimbriata* plant were collected and dried in open-air under a shade 310. The dried material was ground in a swing hammer mill 320. For the extraction step 330, about 500 kgs. of this dry powder material was charged to an extractor. The extractor includes a stainless steel vessel of about 5,000 liters capacity provided with an agitator system and a surrounding jacket for steam heating. About 2,000 liters of about 30% aq. ethanol solvent was charged into the extractor. The solvent charged was formed by mixing about 600 liters of rectified spirit with about 1400 liters of water. The extractor contents were maintained at about 70-75° C. by heating with steam and the extraction was carried out for about six hours. This extract is referred to as "A". The volume of extract "A" was about 1,500 L.

The residue in the extractor comprising the partly-extracted *Caralluma* plant material was subjected to a second extraction (leaching) operation. About 2,000 liters of about 30% aq. ethanol was charged into the extractor and the extraction carried out at about 70-75° C. The extract was taken out of the extractor. The quantity of extract obtained was about 1,500 L. This extract is referred to as "B".

The plant residue in the extractor, comprising the twice-extracted *Caralluma* matter was subjected to the third extraction. About 1,500 L of about 30% aq. ethanol solvent was charged into the reactor(extractor) to yield about 1,500 L of extract at the end of the extraction operation which was carried out at about 70-75° C. This extract is referred to as "C".

For the first concentration step 341, the extracts "A" and "B" were both separately concentrated in concentrators down to a volume of about 150 L each. The extract "C" was used as solvent charge (solvent feed) for the first stage extraction of the next batch of *Caralluma* plant material. In this example, the solvent charge in the first extraction is solute-free aq. ethanol of about 30% strength. In the normal course, the solvent charge to the first extraction would be the "C" extract obtained from another batch. But being a freshly commenced extraction operation, the "C" extract was yet to become available and hence solute-free solvent was used.

At this stage, the concentrated extracts "A" and "B" are combined giving about 300 L of material (the step 344). This was filtered in a stainless steel Nutsche type Filter using Hyflosupercel as filter aid (the step 350). The filter bed was washed with about 50 L of about 30% aq. ethanol.

The filtrate contains the glycosides. About 300 L of n-hexane is added to the glycosides solution to dissolve out and remove the resinous matter therein (the step 360). After allowing a period of time for the hexane to dissolve the resinous matter the material-in-process was subjected to a separation operation 370 resulting in the separation of a light hexane-rich layer and the heavier glycoside solution. The hexane-rich layer was sent for hexane recovery while the glycoside solution layer was subjected to another treatment with n-hexane. Again about 300 L of hexane was used. The separation procedure was repeated giving the two layers out of which the lighter hexane layer was sent for hexane recovery and the heavier glycoside layer was sent for the second concentration step 342 where concentration was carried out in a thin film evaporator at about 45° C. and under a vacuum of less than 20 mm. of Hg. The concentrated material constituted the first *Caralluma* extract product. The above procedure was carried out five times to check whether the yields are reproducible. The amount of product obtained ranged between 55-65 kgs. The composition/analysis of the product obtained is given hereinbelow.

TABLE 5

Product: First *Caralluma* Extract
(From *Caralluma fimbriata*)

| Test Parameters | Specification | Actual Values |
|---|---|---|
| Appearance | Brown to dark brown liquid | Complies |
| Solubility in water | Soluble | Soluble |
| Total dissolved Solids | 65% minimum w/w | 71% w/w |
| Total Bitters | 1.5% minimum w/w | 2% w/w |
| Total Saponin glycoside | 5% minimum w/w | 7% w/w |
| Total Pregnane Glycosides | Above 15% w/w | 19.6% w/w |
| Resinous matters | Not more than 0.5% w/w | 0.05% w/w |
| Total microbial count | 5,000 cfu/gram max | 25 cfu/g |
| E. coli & Salmonella | Absent | Absent |
| Coliforms | Absent | Absent |
| P. Aeruginosa | Absent | Absent |
| S. Aureus | Absent | Absent |
| Heavy metals | 10 PPM maximum | Complies |

Example 2

The solid type *Caralluma* extract product of the invention was prepared starting with the product of Example 1.

About 60 kgs. of the product obtained in Example 1 was mixed with the required quantity of maltodextrin, starch and gum acacia in a mixer and blended for about 30 minutes to get a homogeneous mass (the step 410).

The homogeneous mass was dried in a tray drier. The material was spread in a thin layer over the stainless steel trays of the drier and dried at a temperature of about 60° C. (the step 420).

The dried product from the foregoing step was powdered by, for example, a micropulverizer (the step 430) and then sifted in an S. S. Sifter to a particle size of about 40-80 mesh (the step 440). The sifted material was blended in a double cone blender for about one hour to get a homogeneous powder (the step 450).

The homogeneous powder was the second *Caralluma* extract product of the invention. The abovementioned procedure was repeated five times. The analysis range of the product obtained is given hereinbelow.

TABLE 6

Product: Second *Caralluma* Extract (Standardized)
(from *Caralluma fimbriata*)

| Test Parameters | Specification | Actual Values |
|---|---|---|
| Appearance | Brown to dark brown powder | Complies |
| Solubility in water | 75% minimum w/w | 97.0% w/w |
| Loss on Drying | 10% maximum w/w | 2.8% w/w |
| Total Bitters | 3% minimum w/w | 6.3% w/w |
| Total Saponin glycoside | 10% minimum w/w | 17.8% w/w |
| Total Pregnane Glycosides | Above 30% w/w | 55.2% w/w |
| Resinous matters | Not more than 1% w/w | 0.15% w/w |
| Total microbial count | 5,000 cfu/gram max | 25 cfu/g |
| E. coli & Salmonella | Absent | Absent |
| Coliforms | Absent | Absent |
| P. Aeruginosa | Absent | Absent |
| S. Aureus | Absent | Absent |
| Heavy metals | 10 PPM maximum | Complies |

Example 3

The same steps as outlined in the embodiment 2 were followed with the following differences. In Example 3, drying was conducted in a spray drier instead of a tray drier, and the homogeneous mass was dissolved in water as is required for feeding to a spray drier. The minimum quantity of water was used.

The spray dried *Caralluma* extract was found to be finer and more uniform in size and consequently it was not necessary to carry out the optional steps of powdering and sifting.

Example 4

100% methanol was used as solvent with the resin dissolving solvent, n-hexane, to make the *Caralluma* extract starting with *Caralluma* plant material. The yield of glycosides was relatively low in comparison to the use of 30% aq. ethanol as in embodiment 1. n-Hexane consumption was high because of the higher amount of the resins extracted out by 100% methanol.

Methanol solvents of strengths 60%, 70%, 80% and 90% were also used. The observations of the inventors for these methanol concentrations are generally as for 100% methanol.

Example 5

Aqueous methanol of 30% strength was used. The yield of glycosides was better than for the higher strengths. The yield is optimum at around 30% strength of methanol and is comparable to that for 30% aq. ethanol under comparable conditions. The product was the first *Caralluma* extract and the resin dissolving solvent used was n-hexane. A tray drier was used for drying.

Example 6

Extraction was done with ethylene dichloride as solvent to produce the second *Caralluma* extract. The optional resin removal step was carried out for which n-hexane was used. Adsorption was done on maltodextrin. The product was found to be hygroscopic. The glycoside yield was lower than with 30% aq. ethanol solvent under similar conditions.

Example 7

Aqueous methanol of 30% strength was used as the extraction solvent and n-hexane was used for resin removal. The product was the second *Caralluma* extract. Spray-drying was adopted. The yield was equivalent to that of 30% aq. ethanol under comparable conditions. The product was hygroscopic.

Although the present invention has been described in considerable detail with reference to certain preferred versions thereof, other versions are possible. Therefore, the spirit and scope of the appended claims should not be limited to the description of the preferred versions contained herein.

Effects of Pregnane Glycosides and the *Caralluma* Extracts

Although some limited and non-conclusive tests and animal trials appear to have been done in the past on some medicinal properties of *Caralluma*, neither test nor animal or human clinical trials appear to have been conducted on the appetite-suppression property or on weight reduction and other obesity symptoms related properties of pregnane glycosides.

The medicinal and health effects of pregnane glycosides identified by the present inventors include a treatment of obesity, a reduction of blood glucose, a reduction of blood pressure, a reduction in hip, waist and arm circumferences, a reduction of fat, an increase of BMR, a decrease of BMI, an increase of lean body mass, an appetite-suppression and a reduction/elimination of joint pain. Some of the effects are interrelated and are interdependent.

In addition to the abovementioned ten effects, this invention also deals with other related effects such as anti-aging, a treatment for falling sex drive and an enhancement of energy levels.

The properties have been established by carefully designed and conducted animal trials and subsequently clinical trials on human subjects. This invention is also the first in correlating the properties to the pregnane glycosides of *Caralluma*.

Preferably, the glycosides are caratuberside and/or bouceroside or mixtures thereof including the isomers thereof. More preferably, the compositions for the treatment related to the medicinal and health effects are mixtures of caratuberside and bouceroside which are found to exhibit strong synergy effects particularly for treatment and management of obesity and obesity-related disorders/symptoms. Preferably, the mixture has caratuberside content from about 90% to 95% w/w.

Two isomers of caratuberside and ten of bouceroside are known to be present in *Caralluma*. The glycosides may be in their unconverted forms or in the form of any of the pharmaceutically accepted salts. The pharmaceutically acceptable carriers may be used with the glycosides which may be in their converted or unconverted forms.

Instead of using the *Caralluma* extracts, it would be possible to isolate any of the pregnane glycosides in a pure form and then use them either singly or as mixtures. Alternatively, the glycosides may be obtained by synthesis methods. As the caratuberside-bouceroside ratio (CBR) found in the *Caralluma* species is almost equal to the value at which the synergy is a maximum, it is advantageous to directly employ a *Caralluma* plant extract such as the first *Caralluma* extract and the second *Caralluma* extract in the treatments.

*Caralluma* plants also contain some saponin glycoside compounds which are present in small quantities and which are precursors of a number of usefull products. However, since their role in the treatment is insignificant except for one application discussed hereinbelow, the saponin glycoside compounds could therefore be left substantially unextracted when preparing the *Caralluma* extracts for the treatment.

The term 'glycoside' is therefore used in the further specification hereinbelow to refer to the pregnane glycosides unless otherwise required by the context.

*Caralluma* plant matter also contains bitters which are also of significance medically and healthwise wherein the pregnane glycoside includes some amounts of the saponin glycoside and/or bitters.

The *Caralluma* extracts such as the first *Caralluma* extracts and the second *Caralluma* extracts made by the above processes are easily convertible into any of the pharmaceutically acceptable forms, such as tablets, capsules, suspensions and injections. The conversion of the glycosides in the *Caralluma* extracts into the form of any of the pharmaceutically acceptable salts may also be easily carried out if required. The conversion may be carried out by any of the known processes.

Unlike the conventional treatments of the obesity, the pregnane glycosides act without interfering with the digestion process or thermogenesis or neurotransmitter levels. The *Caralluma* extract containing pregnane glycosides acts on the Kreb's cycle (citric acid cycle) at critical points thereof to inhibit the fat synthesis in the liver and other cells of the subject and to enhance fat burning (a fat metabolism).

It is believed that the pregnane glycosides also act on the hunger center in the brain and reduce the feeling of appetite. Remarkably, this action occurs without any side effects. The pregnane glycosides are believed to suppress appetite without causing any significant disturbance in the neurotransmitter levels or their functioning, unlike the conventional appetite-suppressants. These inventors have further found that pregnane glycosides also apparently increase thermogenesis without manifestation of any side effects observed with the known thermogenesis enhancers.

The glycosides have been tested to be nontoxic and generally free of side effects. In cases where side effects were observed during the tests they were only gastro-intestinal (GI) in nature and were minimal and transient. The side effects generally disappeared within about a week from the commencement of the treatment.

Unless otherwise specified, the term '*Caralluma* extract' in reference to the compositions of the invention herebelow refers to a 30% w/w extract, that is, it contains 30% by wt of a mixture of pregnane glycosides. The mixture of glycosides is to be understood to contain caratuberside and bouceroside (including their isomers) to the extent of 99% and above. The caratuberside-bouceroside ratio (CBR) of the composition is preferably from 9:1 to 11:1.

Thus, this invention provides for novel uses of pregnane glycosides and/or *Caralluma* extracts in the treatment and management of obesity and obesity related disorders/symptoms and other disorders/symptoms wherein glycosides and/or extracts are administered to achieve weight reduction, reduction of BMI, reduction of fat, reduction in waist, hip and arm circumferences, reduction of blood glucose, reduction of blood pressure, increase of lean body mass, increase of BMR, reduction in blood cholesterol, enhancement of the blood HDL/LDL ratio, appetite suppression, enhanced stamina, energy and endurance levels, improved hearing, improved capillary health, improved cognitive and memory function and/or for treatment and management of clinical depression, migraine, osteo-arthritis, aging syndrome, menopausal syndrome, mood elevation and joint inflammation and to improve/regulate these parameters/conditions/functions.

According to the invention, therefore, there is provided the use of pregnane glycoside(s)(PG) in the form of extracts of the *Caralluma* species of plants or otherwise, either singly or as mixtures thereof, in the treatment and management of symptoms/disorders such as obesity, migraine, osteo-arthritis, overweight, clinical depression, hearing loss, a sexual dysfunction, high BMI, low BMR, hyperglycaemia, hypertension, hypercholesterolemia, low stamina, endurance and energy levels, reduced cognitive and memory functions, capillary degeneration, joint inflammation/degeneration, menopausal syndrome, aging syndrome, circulation syndrome and others; in the alteration/improvement/regulation of parameters/conditions/functions such as appetite levels, weight, BMI, BMR, waist, arm and hip circumferences, fat levels, lean body mass, blood sugar, blood pressure(bp), total blood cholesterol, blood HDL to LDL ratio, stamina, energy and endurance levels, cognitive and memory function, mood, circulation, capillary health, hearing, aging, joint mobility, sexual power, drive, stamina and libido; and in skin nourishment and as an anti-oxidant, anti-inflammation and anti-depressant agent, treatment and management and alteration/improvement/regulation comprising the administration of an effective daily treatment(main) dose(s) thereof to the subject over an adequate period of time followed optionally by a daily maintenance dose(s) thereof over an extended period of time or indefinitely, the pregnane glycoside content of main and maintenance doses being specified by the molecularly equivalent amount of caratuberside(CTB) therein, pregnane glycoside(s) optionally including the saponin glycoside(s) and/or the bitters of *Caralluma* species and being optionally supplemented by one or more additional therapeutical, nutraceutical or nutritional components.

According to the invention, there is, further, provided methods for the treatment and management for disorders/symptoms and for the alteration/improvement/regulation of parameters/functions/conditions mentioned hereinabove.

Still further, according to the invention, there are provided pharmaceutical compositions containing pregnane glycoside(s) in the form of extracts of the *Caralluma* species of plants or otherwise, for the treatment and management of disorders/symptoms and for the alteration/improvement/regulation of parameters/functions/conditions, comprising pregnane glycoside(s) and optionally including therein the saponin glycoside(s) and/or the bitters of the *Caralluma* species of plants and furthermore, optionally comprising one or more additional therapeutical, nutraceutical or nutritional components.

Still further, according to the invention, there are provided processes of admixture for making pharmaceutical compositions.

This invention also provides for novel food supplement compositions containing glycosides and/or extracts for use in regulation of weight and other obesity-related parameters and other parameters/functions/conditions. In addition to glycosides and/or extracts, supplements may comprise first, second and further additional components that enhance the performance of glycosides and/or extracts, synergistically or otherwise, or that complement extracts/glycosides in terms of the action thereof on one or more of symptoms/disorders or parameters/functions/conditions or in providing additional nutrition. This invention provides for novel uses of food supplement compositions and for methods of use thereof. Within the scope of the invention supplements may contain one or more additional components, that is, in addition to pregnane glycoside(s).

The uses and methods of this invention may be adopted for control/regulation of one or more parameters/conditions/functions to particular, or desired values and also to correct those that have deviated and require to be brought in line with the particular/desired values.

The present invention has found that the dosages of 10 mg to 1500 mg of caratuberside or caratuberside-bouceroside mixtures per day do not exhibit any toxicity or side effects except for the transient effects experienced by some subjects. In the clinical trials that are described further hereinbelow, the dosage was 300 mg per day of the caratuberside-bouceroside mixture of the ratio of the two components(CB Ratio) therein being from about 9:1 to about 19:1. The higher dosages of about 450 mg per day per subject were subsequently adopted. The increased dosages resulted correspondingly in increased changes in the parameter(s), all other things being equal. This result indicates that the dosages and the effects are generally proportional. These inventors observed that this proportionality of the dosages and the effects extends up to at least the dosage of 1500 mg per day. Thus, the dosage to obtain desired speeds of transformation of parameters/functions/conditions can be designed.

The tests/trials were conducted at the established and recognized medical institutions. In India, the trials were done at the St. John's Medical College & Hospital at Bangalore, India under the direction of Prof. Ms. Anura V. Kurpad, M.D., Ph.D., Dean, Institute of Population Health & Clinical Research, Bangalore, India. The US trials were under Dr. Ronald W. Lawrence and Dr. Suneeta Chaudhary of the Western Geriatric Research Institute, Los Angeles, Calif., USA. Other tests have established the effectiveness of pregnane glycosides in reducing/eliminating arthritic pain.

At the completion of the test at Bangalore, India the subjects expressed desire to continue with the *caralluma* extract doses. The tests and the extended Bangalore tests and other tests have established the effectiveness of pregnane glycosides in reducing/eliminating arthritic pains/aches, reducing blood sugar, reducing BP and effecting changes in other parameters/functions/condition mentioned hereinabove. They have established the efficacy of pregnane glycosides in the treatment/management of the obesity-related symptoms/disorders and other disorders/symptoms and in the alteration/improvement/regulation of various parameters/functions/conditions.

A mutagenicity study(Reverse Mutation Test on *Caralluma* extract) by *Salmonella typhimurium* was conducted by M/s. Intox Private Ltd., of Dist. Pune, Maharashtra, India under Dr. P. Y. Naik, Director and Dr. N. S. Deshmukh, Study Director. The study was in accordance with the OECD Principles of Good Laboratory Practices(OECD, 1998) and OECD Guidelines for Testing of Chemicals, Section 4, No. 471 adopted 21 Jul. 1997. The study concluded that *Caralluma* extract is Non-Mutagenic in *Salmonella typhimurium* strains TA 1535, TA 97A, TA 98, TA 100 and TA 102.

A report on the risks and efficacy of *caralluma* extracts based on the abovementioned animal and human studies and other evidence on *caralluma* was commissioned from Dr. Harry T. Preuss, M.D., M.A.C.N., C.N.S., Prof. Of Physiology, Medicine and Pathology, Georgetown University Medical Centre, Washington D.C. 20057, USA. The report notes:

the absence of any adverse event reports on *caralluma* from the Indian subcontinental area where *caralluma* has been a part of the food chain for several population groups over hundreds of years, the average daily intake by the population groups ranging from about 100 grams to about 400 grams of *caralluma* plant matter, that apparently no alteration of the chemical nature of the *caralluma* principles occurs during the process of extraction of the plant matter by aq. ethanol, the heavy metal content of *caralluma* extracts was found to be quite low and well within limits based on several separate investigations, that various tests indicate extremely low amounts(well within safe limits) of hexane, methanol, 2-propanolol, chloroform, 1,4-dioxane, methylene chloride and trichloroethylene in *caralluma* extracts, that the 2 month long test program at Bangalore, India referred to hereinabove is suggestive of weight loss although the differences were not significant in magnitude. However, that there was a significant drop in waist circumferences suggesting that a part of the fat loss must have been masked by muscle build-up, that tests on various categories of diabetic mice clearly show significant lowering of blood glucose levels through an 'insulin-like' action, that is, by increased release of insulin and/or sensitisation of the animal to lesser amounts of insulin, that *caralluma* extracts have anti-nociceptive and anti-inflammatory action in addition to anti-hyperglycaemic property.

The mechanism of the action of pregnane glycosides in producing the effects is not at present fully understood, and more work is required to ascertain and establish the same. However, the general outline of the mechanism is understood in which context these inventors make the following observations. It may be again mentioned here at this point that the link between the pregnane glycosides and the effects is conclusively established by the statistical evidence of the trials.

The biochemical processes of carbohydrate, protein and fat metabolisms, and of the breakdown and biosynthesis of fats relevant to the subject of this invention are summarized below.

Carbohydrates, proteins and fats are broken down in cells to generate energy in the form of energy carrying molecules such as ATP(Adenosine Triphosphate). The breakdown also produces pyruvic acid that diffuses into the mitochondria where a series of reactions produces, inter alia, acetyl coenzyme A and oxaloacetate. Compounds NAD and FAD are also produced. They carry activated hydrogen atoms that subsequently take part in fat synthesis reactions. A further reaction links acetyl coenzyme A and oxaloacetate to give a molecule that is capable of diffusion across the mitochondrial wall into the cell cytoplasm. The NAD and FAD also diffuse out into the cytoplasm where, together with acetyl coenzyme A, they undergo various reactions ending with the synthesis of fat molecules.

In the cytoplasm, an enzyme called citrate lyase catalyzes the breakdown of the combined molecule into its constituent parts, oxaloacetate and acetyl coenzyme A. The action of citrate lyase is critical in that blocking the action thereof would prevent formation of acetyl coenzyme A in the cytoplasm and thereby disrupt the fat synthesis process in the cells.

The precursor (building block) of fat synthesis in the cells is malonyl coenzyme A which is produced from acetyl coenzyme A. Malonyl coenzyme A is a key to fat synthesis in cells and, if the production of malonyl coenzyme A is either prevented or restricted, the fat synthesis is similarly affected.

Both a fat breakdown (a fat metabolism) and a fat synthesis occur simultaneously in cell cytoplasm particularly in liver cells. The fat breakdown is promoted (catalyzed) by an enzyme called carnitine acyltransferase. Relative levels of carnitine acyltransferase and malonyl coenzyme A determine the balance between the twin reactions of fat synthesis and breakdown.

Acetyl coenzyme A is also consumed in the mitochondria to generate/release energy. Only when the energy requirements of a cell are met, the excess acetyl coenzyme A gets formed that migrates to the cytoplasm where it partakes in the fat synthesis as mentioned above.

An important factor is the feeling of satiety/hunger that arises in the hypothalamus. The hypothalamus receives signals from the stomach conveying the position, that is, the fullness or otherwise of the stomach. This is translated into the appropriate feeling of hunger or satiety in the brain. Via another channel the brain also receives signals indicating the position about glucose and glycogen levels in the liver. If these levels are high, they generate a feeling of satiety in the brain and vice versa.

The present inventors observed that pregnane glycosides block the action of the citrate lyase and/or direct its action away from splitting the combined acetyl coenzyme A-oxaloacetate structure. The resultant drop of acetyl coenzyme A levels in the cytoplasm decreases fat synthesis. These inventors further believe that pregnane glycosides inhibit the action of malonyl coenzyme A in fat synthesis. Thus, pregnane glycosides provide two-fold action in decreasing fat synthesis, one by decreasing the formation of malonyl coenzyme A and the other by inhibiting the action of malonyl coenzyme A generated.

The decrease of malonyl coenzyme A levels shifts the malonyl coenzyme A-carnitine acyltransferase balance in favor of the fat breakdown as opposed to the fat synthesis. Thus, under the effect of pregnane glycosides, a body not only decreases fat synthesis but speeds up the fat breakdown (the fat metabolism). The effect is greater release of energy, that is, an enhancement of BMR. The latter effect is more significant because the scope of the decrease in fat synthesis is quite small in view of the fact that the amounts of fat synthesized by a body in a day are a fairly small quantity. The increased fat metabolism and the increase of BMR make a subject feel more energetic pregnane glycosides are therefore energy enhancers and increase stamina.

The pregnane glycosides also act on the hypothalamus to generate a feeling of satiety and well-being and reduce the feeling of hunger. This occurs without any side effects such as those associated with known appetite-suppressants.

Pregnane glycosides also act in the liver to direct the lipids towards glycogen production. Increased glycogen level also contributes towards the reduction in the feeling of hunger felt by a subject.

This mechanism of the action of pregnane glycosides in relation to obesity and obesity-related symptoms/disorders and parameters/conditions/functions has apparently not been known/presented before in the prior art. The description given hereinabove establishes the effects of the pregnane glycosides in relation to the various symptoms/disorders/functions/ parameters/conditions associated with obesity. The basis of the effects in relation to obesity and obesity-related symptoms/disorders is the appetite-reducing, the fat synthesis disruption, the fat metabolism increase and other properties of the pregnane glycosides. Specifically, the obesity and obesity related functions/parameters/conditions/disorders/symptoms that are affected by pregnane glycosides are: weight, obesity, BMR, BMI, blood sugar, BP, blood lipids, appetite, lean body mass, waist, arm and hip circumferences, joints and others. Other properties of pregnane glycosides that come into action are: improving capillary health, anti-inflammatory, anti-oxidant and others.

The further description given hereinbelow establishes the effects of the pregnane glycosides as regards several other non-obesity disorders/symptoms/functions/conditions/parameters. With regard to osteo-arthritis and joint degeneration/inflammation, these inventors observe that the action of pregnane glycosides is very significant as it provides not only reduction/elimination of the inflammation but also improvement in the health of the joints by reducing/reversing the degeneration of the bone and synovial tissue. Pregnane glycosides have both anti-arthritic and anti-inflammation properties. *Caralluma* extracts, furthermore, cause increased secretion of the synovial fluid which increases joint efficiency and mobility. With pregnane glycosides, morning stiffness is either reduced or eliminated and the joints feel stronger and are able to take up greater loads.

With regard to clinical depression and mood elevation, these inventors observe that pregnane glycosides act through intervention in the neurotransmitter levels. This has not been observed/reported in prior art. The connection between pregnane glycosides and clinical depression and in mood elevation was first observed by these inventors during the clinical trials on the appetite-suppression and weight reducing properties of *caralluma* extracts. It was observed that subjects taking the extracts experienced an increased feeling of well-being, enhanced energy levels, mood elevation and increased tolerance to pain and stress. Clinical depression is characterized by pathological changes in neurotransmitter function, especially catecholamine levels. Significantly, low levels of serotonin(5 hydroxytryptamine, 5HT) have been demonstrated in neurochemical disorders like clinical depression, obsessive-compulsive disorders, social phobia and hypochondria. Serotonin is also apparently involved in the sensation of hunger. These inventors believe that through its effect on the neurotransmitter serotonin and others in the suppression of appetite, pregnane glycoside(s) is able to simultaneously provide mood elevation, increased ability to cope with stress and greater social interests. Unlike the known anti-depressants of the SSRI class(Selective Serotonin Reuptake Inhibitors), pregnane glycosides do not have cardiovascular side effects or others such as dysrhythmia and hypertension. Adoption of SSRI's often results in serotonin intoxication unlike in the case of pregnane glycosides. Serotonin intoxication can cause aggressive/violent or erratic behavior, insomnia and hyperactive state in subjects.

One of the most common form of a sexual dysfunction is primary impotence, that is, an erectile dysfunction(ED). ED is caused by various psycho-physiological factors including depression the effect of which is to restrict or decrease blood flow to the erectile tissue in the penis which is known as the corpus cavernosum. While nitric oxide in blood relaxes the muscles in the penis to let more blood flow in, a phosphodiesterase enzyme called PDE5 inhibits the action of the nitric oxide. Known treatments of ED are based on administering PDE5 inhibitors. However, the action of PDE5 inhibitors is quite slow and furthermore has adverse cardiological effects. It is contra-indicated in cardiovascular patients and for people suffering from low or high BP particularly those on nitrate-based vasodilators. PDE5 inhibitors are also known to induce depression, which itself is a known causal factor in ED. The tests conducted by these inventors have demonstrated that pregnane glycosides increase energy levels in subjects; cause mood elevation and a feeling of well-being. The anti-depressant properties of the pregnane glycosides are also relevant in this context. These inventors observe that while pregnane glycosides are not known to cause directly increased blood flow to the penile tissue, they may be causing the same to happen by virtue of the mood-elevation, energy-enhancing. Capillary health restoring and anti-depressant properties thereof as the tests confirm improvement in sexual function in subjects suffering from ED. Increased fluid secretion in the male and female reproductive organs was also observed by the inventors.

In female subjects, particularly those suffering from age and/or menopausal syndrome, these inventors found that pregnane glycosides generated resurgence of sexual interest and increased libido.

Memory impairment and reduced retention are related to the neurotrasmitter levels in the brain, in particular serotonin levels. Pregnane glycosides, as observed by these inventors, cause enhancement of energy levels, libido and gastro-intestinal motility. They also cause mood elevation. The resultant increase in serotonin levels generates a feeling of well-being, increased perception of pain and stress, increased memory recall and retention, increased speed of retrieval and augmented cognitive function.

This invention has observed that pregnane glycosides cause a reduction of total cholesterol in subjects and also an increase in the HDL/LDL ratio. The mechanism for this action is not understood but the effect mentioned has been demonstrated by the clinical tests described hereinabove.

In the case of migraine attacks, these inventors have found that pregnane glycoside decrease inflammation and pain and increase tolerance to stress and pain. This invention has found that pregnane glycosides increase capillary elasticity and in general ensure capillary health. The anti-depressant and mood elevation property of pregnane glycosides gives a psychological boost to the subject and the higher serotonin levels generated by the glycosides increase the confidence level of the subject in facing up to the migraine attack.

These inventors report that pregnane glycosides enhance energy levels, endurance levels and increase stamina as outlined in the description hereinabove. This action of pregnane glycosides together with reduced fat synthesis and increased fat burning helps build up muscle tissue. Thus, this invention provides for administration of pregnane glycosides for building up the lean body mass. Pregnane glycosides and their formulations are therefore, good diet adjuncts/supplements in sports and athletics training schedules.

As regards diabetes, these inventors observe that pregnane glycosides exhibit dual action: reduction of weight and effect on the lipid metabolism and reducing/regulating blood sugar as established by the tests/trials. The clinical trials have also established the anti-hypertensive and anti-cholesterolemic properties of *caralluma* extracts.

These inventors observe that in view of the energy, stamina and endurance enhancing properties of *caralluma* and its property of restoring elasticity to capillaries is relevant for its use in the treatment of the aging syndrome.

The role of pregnane glycosides in capillary regeneration and protection has been mentioned hereinabove. This forms the basis for the novel use thereof in treating capillary degeneration and maintaining capillary health as provided by this invention.

The role of pregnane glycosides in regenerating capillary walls is also the basis for the novel use of pregnane glycosides in treating loss of hearing as provided by this invention. Pregnane glycosides restore capillary health in the ear region which leads to improvement in the hearing function.

The regeneration of capillary walls helps increase/restore blood flow to the various functional zones in the body. Thus, pregnane glycosides are effective in treatment of a sexual dysfunction in men and women as they enhance blood flow to the various genital and reproductive organs. Pregnane glycosides also enhance the flow of lubricant and other fluids in the reproductive organs and prevent vaginal dryness. Hence, this invention provides for the novel use pregnane glycosides in treatment of a sexual dysfunction, reproductive dysfunction, hearing loss, aging syndrome and others.

The connection between pregnane glycosides and capillary health is also the basis of the novel use thereof in skin nourishment as provided by this invention. Thus, pregnane glycosides can restore and maintain skin health such as of the face, arms and other parts of the body.

The intake of pregnane glycosides by population groups that consume Caralluma as a food may be anywhere up to 1,500 mg per day. Further, an intensive LD 50 safety pharmacological study conducted at the St. John's Medical College and Hospital, Bangalore, India according to the OECD guidelines for testing of chemicals (Acute Oral Toxicity-Fixed Dose Method) showed no mortality in rats upon administration of a very high dose of 5 g per kg body weight of Caralluma fimbriata extract containing about 50% w/w of pregnane glycosides. No fatalities or adverse effects were noted. These data indicate that the toxicity limit of pregnane glycosides is quite high, and may well be as high as 5000 mg per day for humans. This also establishes that accidental overdoses of pregnane glycosides (or Caralluma extracts) do not pose any risk.

The clinical trials program done at the St. John's Medical College and Hospital, Bangalore, India was double-blind, controlled and randomized, and followed the guidelines of the Indian Council of Medical Research, New Delhi, India with regard to methodology and ethical considerations and other factors. Sixty-two obese subjects were selected at random for the test, fifty of whom completed the test, the rest having dropped out during the test. Half of the subjects who completed were on active medicine and the rest were on placebos.

Each subject was examined at the commencement of the trials and then at the end of the first and second months. The examination included anthropometric parameters of body weight, waist circumference, MAC, hip circumference, Fat %, BIA Fat % and lean % and a series of biochemical measurements including blood sugar, lipid profile and others. The subjects were questioned about hunger level, urge to eat, fullness and thoughts on food and their responses recorded.

Both parametric (paired 't' test) and non-parametric tests such as Wilcoxon Signed Rank test (paired analysis) and Mann-Whitney test (for unpaired analysis) were used to look for significant changes between time points and between the groups. Both parametric and non-parametric tests gave similar results.

In groupwise analysis, the Wilcoxon-Signed Rank Test was used to check differences between time points separately in each group. The significant values were based on $p<0.0016$. Paired 't' test analysis was used where differences were looked for in mean values between time points separately in each group. Significant differences were based on $p<0.016$ (a value of 0.05 corrected with Bonferroni correction for three multiple comparisons for each analysis).

In the inter-group analysis, differences in change in each parameter were compared between the groups using Mann-Whitney test for independent comparisons. Significant differences were taken where $p<0.05$.

The overall conclusions from the trials are that statistically significant differences between time points were seen in the active group for the parameters of body weight, BMI, waist circumference, hip circumference, fat loss, blood pressure and hunger levels while blood sugar and lipid profile did not show any significant results.

The doses administered to the subjects consisted of an extract of Caralluma fimbriata. The extract incorporated in the capsules administered in this study was prepared as follows: The aerial parts of the plant were extracted with 30% v/v aq. ethanol. Resin removal was done with n-hexane solvent. This yielded the pregnane glycosides in aq. ethanol solution. This was concentrated and adsorbed on a suitable excipient. The material was then dried and filled in hard gelatin capsules. The dried, adsorbed material contained either 25% or 50% w/w pregnane glycosides. Each capsule contained 500 mg of the excipient adsorbed extract containing either 25% or 50% w/w pregnane glycosides giving capsules of two strengths, single and double. The subjects took two capsules a day, one before each meal. The capsules given to the placebo group did not contain the extract. For some tests involving low value doses, capsules containing 250 mg of the extract containing 25% and 50% w/w pregnane glycosides were used.

The adverse effects observed were gastro-intestinal (GI) in nature and were reported in both the groups, active and placebo. The effects were moderate acidity, mild constipation and mild to moderate flatulence and subsided within a week of commencement of trials. No adverse effects were noted in other systemic functions. No changes in electrocardiogram (ECG) were observed. No sympathomimetic effects were found.

The American study by Dr. Ronald Lawrence and Dr. Suneeta Chaudhary at the Western Geriatric Research Institute, Los Angeles, Calif., USA was done on 26 randomly selected overweight patients of whom 19 were placed in the active group while 7 were on placebo. The trials were done over a 4-week period.

The subjects were taken from two active practices in the Los Angeles area and randomly assigned to the two groups. The age profile varied from 31 to 73. Two subjects dropped out during the trials leaving 24 to complete the test.

The following parameters were measured before and at the end of the tests: weight, height, hip and waist circumference and blood pressure All the subjects were advised to pursue a normal pattern of activity, exercise and food intake and not to alter their diets during the test.

The active group was given gelatin capsules containing an extract of Caralluma fimbriata. The capsules for the placebo did not contain the extract. The subjects were asked to take two capsules a day. The active capsules contained 500 mg of the extract each, the extract containing about 50% w/w of pregnane glycosides.

The extract incorporated in the capsules administered in the US study was prepared as follows. Aerial parts of Caralluma fimbriata were extracted with aq. ethanol and then the extract was subjected to resin removal. The extract was then concentrated, adsorbed on a suitable excipient and the material dried and then incorporated in gelatin capsules.

The American study concludes that the administration of *Caralluma fimbriata* extracts used in the weight reduction program coupled with no change in a daily activity pattern and the diet of the subjects resulted in a statistically significant weight loss over a period of only four weeks. The study noted the lack of toxicity and the absence of any side effects. The study recommends further trials and states that there are few, if any, over-the-counter natural substances which can produce such a weight reduction effect.

At the conclusion of the Indian study, the subjects expressed a voluntary desire to continue with the pregnane glycosides doses. The study was therefore extended and has already run over 12 months and is continuing. This has proved advantageous as the period of the earlier study was only two months. In the continuation study, the dosage has been increased to three capsules a day in a two-plus-one system. The increased dosage and the longer period have given some important insights that were not apparent earlier. Thus, while the earlier test did not show statistically significant effects with regard to the blood sugar of the subjects, the link was clearly evident from the results of the extended study. The extended tests have established that the administration of pregnane glycosides does lead to a reduction of blood sugar levels, reduction of BP, reduction of serum cholesterol and reduction of LDL together with enhancement of HDL cholesterol in blood.

The composition for the treatment may contain the glycosides in the unconverted forms or otherwise. The glycosides, converted or unconverted, may be associated with any of the known pharmaceutically accepted carriers and excipients and furthermore be in the form of any of the pharmaceutically accepted salts. The compositions may further include any pharmaceutically acceptable and/or edible coloring agents, flavoring agents and other additives. Also, the compositions may further include a second component such as a fenugreek extract, glucosamine sulfate, glucosamine sulfate with rutin, a *garcinia* extract, a green tea extract, an ashwagandha extract, and shilajith.

*Garcinia*(*Garcinia cambogia*) extract is a known weight reducing agent. It has been used as a food supplement in India and China over hundreds of years and its nontoxic nature is well established. The active principle of *Garcinia cambogia* is (−)-hydroxycitrate (HCA).

HCA suppresses appetite and inhibits absorption and biosynthesis of fats, cholesterols and triglycerides. A dose of 3 mg of HCA per kg body weight is known to cause about 43% reduction in appetite at 6.5 hours and about 29% at 24 hours and is preferably taken 30 to 60 minutes before meals. The appetite reduction effect is dose dependent and no rebound eating is observed upon stopping of the dose.

The effect of HCA on the brain and the neurotransmitter system in reduction of appetite does not appear to have any side effects. HCA also acts in the upper digestive tract in reducing fat absorption and during the Kreb's cycle to reduce fat biosynthesis. HCA also acts in the liver and diverts carbohydrates from lipid biosynthesis to hepatic glycogen synthesis that also contributes to the feeling of reduced appetite.

It will be observed that there are considerable similarities in the action of the pregnane glycosides and HCA in appetite suppression and weight reduction. This invention therefore, provides for mixtures of pregnane glycosides(or *caralluma* extracts) and *Garcinia* extract (or HCA). The mixtures have been observed by these inventors to exhibit a synergy in the treatment and management of obesity and obesity related symptoms and disorders and in the alteration/improvement/regulation of the obesity related parameters/conditions/functions such as weight, BMI, BMR, waist, hip and arm circumferences, lean body mass, appetite suppression and others. The mixtures increase lean body mass by stimulating thermogenesis without any side effects. The mixtures also mildly reduce systolic and diastolic pressures and reduce cholesterol by inhibiting its production in the liver.

One example of the *Garcinia* extracts that may be used here is as follows:

*Garcinia Cambogia* fruits are extracted with water at boiling temperature several times. The extracts are combined and filtered. It is concentrated to a residual paste and then added to alcohol. It is warmed and filtered. The clear filtrate is distilled to remove the alcohol completely. The concentrated mass is dissolved in a large amount of water and added to Sodium Hydroxide solution to raise the pH level. Calcium salt solution is added to this and agitated for 2 hours. The precipitate formed is filtered, washed with water and dried.

The constituents of this example are given below:
Description: Brown to pale brown powder
Identification: Positive for Calcium
Loss on drying: Not more than 6%
Solubility in boiling water: Almost Soluble
Assay of Hydroxy Citric Acid: Not less than 50%
Content of Calcium: Not less than 18% and not more than 21%
Total microbial count: Not more than 1000 cfu/g
*E. coli* & *Salmonella*: Absent
Heavy Metals: Not more than 10 PPM Glucosamine is known to be used for treatment and relief in arthritis. It gives strength to the cartilage and rigidity to the joints. These inventors found that the mixture of glucosamine with pregnane glycosides(or *caralluma* extracts) is synergistic in the treatment and maintenance of joint health. The mixtures enhance the synthesis of new cartilage and inhibit the action of the cartilage destroying enzymes. The combination is far more effective in reducing joint pain and inflammation and in enhancing joint mobility than the sum of the actions obtainable individually by the two components. Glucosamine may be in the form of the sulphate or any of the other pharmaceutically accepted salts in the compositions disclosed herein.

Rutin is a bioflavonoid that has been used in the treatment of arthritic pain. Rutin is a capillary protectant in that it restores elasticity to capillary walls. Application of Rutin restores blood flow to joints and thereby enhances secretion of the synovial fluid. One of the other bioflavonoids may also be used: Hesperidin, Diosmin or others. This inventor found the synergy in mixtures of pregnane glycosides and Glucosamine and Rutin, mixtures of pregnane glycoside and glucosamine and in mixtures of pregnane glycoside and rutin and provides such mixtures for the treatment and management of osteo-arthritis and in the reduction/elimination of joint inflammation and pains. The mixtures may also include chondroitin. Both Glucosamine sulphate and chondroitin sulphate are acidic and therefore mixtures thereof with pregnane glycosides are problematic for subjects who suffer from gastric acidity. For such subjects, this invention provides for mixtures of pregnane glycosides and Rutin or one of the other bioflavonoids.

Green Tea extract has been known for use as an anti-oxidant, anti-aging, anti-microbial, anti-viral, anti-fungal and an anti-cancer agent. It has been also used in plasma cholesterol control and for control of blood glucose and insulin levels. Green tea extract also inhibits the accumulation of fat in the body and the liver in particular. Its pre-eminent use is as an anti-aging agent. Pregnane glycosides are also anti-oxidation agents in their own right. Pregnane glycosides provide an energy boost, prevent/minimize joint pains and ensure capillary health. Green tea contains polyphenols that are also referred to as catechins. The major catechins in green tea extracts are: epicatechin, epigallocatechin, epigallocatechin gallate (EGCG) and epicatechin gallate. EGCG is the strongest anti-oxidant of the four and is known to cure free radical damage, prevent bacterial infection and reduce cholesterol. These inventors have found that mixtures of pregnane glycosides together with the saponin glycoside found in *caralluma* and green tea extract are synergistic with regard to treating and fighting the aging syndrome, maintaining youthful elasticity in tissues, in slowing down or preventing cataract formation and for increase of stamina, energy and endurance and BMR. The mixtures are excellent anti-oxidant and anti-aging agents.

One example of the green tea extracts that may be used for the present invention can be made by the following process and can have the following constituents.

Green Tea leaves are dried under shade gradually and powdered. It is extracted with Alcohol and water mixture at hot temperature several times. The extracts are combined and filtered. It is concentrated to a specific volume and added to Ethyl acetate. It is agitated in a liquid—liquid extractor till all the Catechins are extracted into Ethyl Acetate.

Separate the Ethyl Acetate layer and concentrate it to a residue under vacuum. Dissolve this in water and spray-dry it or dry it in a tray drier to get a powder. The constituents of this example are given below:
  Description: Brown to greenish brown powder, hygroscopic
  Identification: Positive for bitter taste
  Loss on drying: Not more than 6%
  Solubility in water: Soluble
  Content of Catechins: Not less than 40%
  Total microbial count: Not more than 1000 cfu/g
  *E. coli* & *Salmonella*: Absent
  Heavy Metals: Not more than 10 PPM Ashwagandha(*Withania somnifera*) is known as an aphrodisiac and sexual potency enhancer. These inventors observe that pregnane glycosides are steroidal in nature with close resemblance to sex hormones and believe that pregnane glycosides may be the precursor or a link in the synthesis of vital sex hormones in the body. This invention has discovered that combinations of pregnane glycosides and the withanolides of Ashwagandha are synergistic in respect of their application as aphrodisiacs and enhancers of sexual power and potency. The application as aphrodisiacs and for increasing sexual potency and power relates to both sexes. This invention, therefore, provides for the combinations for enhancing sexual power and potency, as aphrodisiacs, for improvements in the functioning of reproductive organs in both sexes and for treatment of ED. These inventors observe that compositions of pregnane glycosides and Ashwagandha are anti-depressants and are provided by this invention for treatment and management of clinical depression.

One example of the Ashwagandha extracts is made by the following process. Ashwagandha roots are powdered and extracted with a mixture of Alcohol and water at hot temperature several times. The extracts are combined and distilled out to remove alcohol. This mass is dissolved in water, filtered and spray-dried.

The constituents of this exemplary extract are given below:
  Name: Ashwagandha Extract
  Description: Brown to dark brown powder
  Identification: To comply with Standard
  Loss on drying: Not more than 6%
  Solubility in water: Soluble
  Assay of Total Withanolides: Not less than 1.5%
  Assay of Total Alkaloids: Not less than 1%
  Total microbial count: Not more than 1000 cfu/g
  *E. coli* & *Salmonella*: Absent
  Heavy Metals: Not more than 10 PPM Shilajith, also known as Asphaltum or Mineral pitch, is a strong aphrodisiac and sex drive enhancer. This invention reports that mixtures of Shilajith and pregnane glycosides also exhibit a synergy. This is in respect of application of the combination as an aphrodisiac; for curing primary impotency and for increasing sex drive and libido. Mixtures of Shilajith and pregnane glycosides are provided by this invention for the application.

The second component may be shilajith. The shilajith is a strong aphrodisiac, and increases sex drive. There is also synergy between the *Caralluma* extract and shilajith. Shilajith is an exudate from rocks found at high altitudes and is also known as Asphaltum or Mineral pitch. It is a dark red gummy bituminous material formed during compaction of vegetable organic matter.

One example of shilajith that may be used here is as follows. The rock exudates of crude Shilajith are washed with alcohol and water at hot temperature. It is filtered and treated with acidic water. It is washed again with alcohol and dried. The constituents of this product are given below:
  Description: Brown to grayish brown powder
  Odour: Characteristic
  Loss on drying: Not more than 8%
  Assay o Fulvic Acid: Not less than 25%
  Total microbial count: Not more than 1000 cfu/g
  *E. coli* & *Salmonella*: Absent
  Heavy Metals: Not more than 10 PPM Fenugreek extract is known to be effective in reducing blood sugar and is used in anti-diabetic formulas. The component therein which is active in this respect is 4-hydroxy-iso-leucine. This invention explored mixtures of fenugreek extract and pregnane glycosides together with the bitters of *caralluma* for application in reducing blood sugar, in particular FBS(Fasting blood sugar) and found that such mixtures exhibit a synergy and are highly effective in reducing and controlling blood sugar. The mixtures are very relevant for Type 2 diabetic subjects and for those desiring reduction and/or regulation of blood sugar. Both the components are consumed as food products and are therefore, totally nontoxic and safe even at very high doses. These inventors have found that as the dosages are increased the FBS reaches a floor level of about 70-80 mg/dL and does not fall below the level. A combination of about 250 mg of *caralluma* extract containing about 125 mg of the pregnane glycosides together with 250 mg of Fenugreek extract containing 40% 4-hydroxy-iso-leucine taken over a period of about 6 months brought the FBS down from about 160 mg/dL to about 80 mg/dL. This invention therefore, provides a mixture of pregnane glycosides, fenugreek extract containing 4-hydroxy-iso-leucine, *Coccinia* extract containing about 10% terpenes, Bitter gourd extract containing about 8% bitters and Cinnamon extract containing about 15% polyphenols.

Fenugreek also contains protodioscin that is a precursor to many sex hormones including Androgen that stimulates sex urge in men. The role of pregnane glycosides in treating a sexual dysfunction and for increasing sex drive, power and stamina and enhancement of libido has been discussed hereinabove. This invention finds that combinations of pregnane glycosides and protodioscin are synergistic in treating the aspects of a sexual dysfunction mentioned hereinabove. Thus, this invention provides for mixtures of pregnane glycosides and fenugreek extract containing about 50% protodioscin for the treatment for a sexual dysfunction symptoms and/or for enhancing sex drive, power, stamina and libido.

One example of the fenugreek extracts that can be used for this present invention was made by the following process. Fenugreek seeds were crushed to 10-40 mesh and heated with steam to distill out the fenugreek oil. The deoiled seed material is extracted with alcohol repeatedly under hot conditions to get Fenugreek extract. This is dissolved in water and agitated for 3 hours at hot temperature. It is filtered using inert filter aid. The filtrate is concentrated under vacuum and the concentrate is spray dried to get the Fenugreek Extract in a powder form. The constituents of this extract are as follows:
Description: Brown to dark brown powder, hygroscopic
Identification: To comply with Standard
Loss on drying: Not more than 6%
Solubility in water: Soluble
Assay of Steroidal Saponins: Not less than 40%
Assay of 4-hydroxy Isoleucine: Not less than 15%
Total microbial count: Not more than 1000 cfu/g
*E. coli* & *Salmonella*: Absent
Heavy Metals: Not more than 10 PPM This invention provides for an anti-cancer composition that neutralises certain carcinogens and comprises pregnane glycosides with zinc monomethionine, citrus bioflavonoids and selenium as selenium chelate. The mixture exhibits synergy.

The novel composition of pregnane glycosides together with zinc monomethionine and citrus bioflavonoids and selenium as selenium chelate can be also used for the treatment and management of the menopausal syndrome. The composition, which is also synergistic, provides relief from hot flushes and menopausal distress.

The novel composition of pregnane glycosides together with zinc monomethionine and citrus bioflavonoids and selenium as selenium chelate can be also used for skin nourishment. The composition exhibits synergy and protects cell membranes and tissues and ensures capillary health. It is helpful in maintaining youthful elasticity in tissues by preventing the hardening thereof. It is an excellent anti-aging and anti-oxidant composition. It also slows/prevents formation of cataract. The selenium in the abovementioned mixtures may also be as sodium selenate or selenomethionine.

A few other additional components incorporated in compositions provided by this invention are:

A *coccinia* extract containing about 10% terpenes, a bitter gourd extract containing about 8% bitters, a *Hibiscus Subdariffa* extract containing about 25% polyphenols, a cinnamon extract containing about 25% polyphenols, and a *Commiphora Mukul* extract containing about 3% gugulsterones.

A few plant extracts contain components that supplement or enhance estrogen levels in women and are therefore suitable for treatment of menopausal syndrome wherein women suffer hot flushes, depression, night sweat, irritability emotional changes and other symptoms. Combinations of these plant extracts and pregnane glycosides were found by the present inventors to offer synergy in treatment of menopausal problems and in lowering the risk of cardiovascular disease and osteoporosis in post-menopausal women. The plant extracts are: a liquorice extract containing about 5% triphytoestrogen, a red clover extract containing about 8% isoflavones, a Hop's flower extract containing about 5% triphytoestrogen and a pomegranate extract containing about 10% ellagic acid.

Bamboo silica is known to help in osteo-arthritis. This invention has also investigated mixtures of pregnane glycosides with Rutin and bamboo silica and finds them synergical and beneficial in the treatment and management of joint degeneration and inflammation. A mixture of the pregnane glycosides together with glucosamine and Rutin and furthermore containing bamboo silica is also provided by this invention for the treatment and management of joint problems and for maintaining joints health and flexibility.

With reference to the various plant extract additives discussed hereinabove and hereinabelow, it may be noted that a certain value has been specified in each case for the amount of the active component therein. It may be noted that other values for the active components content are within the scope of the invention as the amount of the extracts going into the mixture can be easily adjusted to take into account the percentage content of the active components. The term 'main dose' has been used herein at some places to refer to treatment doses as opposed to the maintenance doses. The terms 'main dose' and 'treatment dose' are, therefore, used interchangeably in this specification.

The uses, methods and compositions and formulations provided by this invention are described hereinbelow.

1. Obesity:

1.1 For subjects of either gender suffering from clinical obesity with a BMI of about 25 to 30, Type 2 diabetes or normal, normotensive or mild to moderate hypertension with no systemic dysfunction, the subject being preferably on controlled diet and/or moderate physical activity, otherwise no restriction.

Main Dose: About 250-500 mg of caratuberside(CTB) per day over a period of 3 to 4 months followed by an optional maintenance dose of about 125-250 mg CTB per day for about six to eight months. The maintenance dose may be taken over an extended period or indefinitely without any adverse effects as *caralluma* pregnane glycosides are good anti-oxidants, nontoxic and well-tolerated nutritional supplements.

1.2 For subjects of either gender suffering from clinical obesity with a BMI of about 30 to 50, Type 2 diabetes or normal, normotensive or mild to moderate hypertension with no systemic dysfunction, the subject being preferably on controlled diet and/or moderate physical activity, otherwise no restriction, a treatment dose double that provided above for the lower BMI category of subjects and optional maintenance dosage the same as for the lower BMI category is provided all other parameters including the period for the doses being the same as for the lower BMI category.

1.3 An alternative schedule for the maintenance dose is to take the same for a period of about 4-5 months and then stop the same for a period of about 6 months. The maintenance dose may be again started at the end of the 6 month period and continued for about three months. The maintenance course may be continued under this sequence of six and three months for an indefinite period. The water intake should be double of the normal during the treatment. During the treatment one-half hour brisk walks in the morning and evening, and diet control, are advised.

By about the fifth week, subjects start feeling the lessening of appetite and of the thoughts of food and simultaneously feel more energetic. Appetite is experienced by the subjects at appropriate times but is satisfied with lesser amounts of food. From this point onwards, weight loss also begins to become quite apparent. By the ninth week, the effects will be clearly apparent in weight loss, appetite reduction, reduction of waist, hip and arm circumferences and other parameters. The waist circumference would be down by at least about 50 mm(two inches) and the weight by at least 3-4 kgs.

1.4 An alternative treatment for obesity provided by this invention comprises a mixture of pregnane glycoside and HCA.

Main dose: About 120-240 mg of CTB with 150-300 mg of HCA per day over a period of about six months. Optional Maintenance dose: the same as the main dose. Period: extended period to indefinitely.

*Garcinia* extract may be used in place of HCA.

In the case of subjects where the gelatin of the capsules causes adverse GI reactions, the dose may be incorporated in a beverage and consumed in the liquid form. This applies to all of the treatments mentioned in this specification. This invention provides for a number of health-ensuring and nutraceutical compositions containing pregnane glycoside and other components, the compositions being provided in both solid and beverage forms.

2. BMR:

2.1 For subjects undergoing moderate physical activity and desiring increase in BMR and energy, endurance and stamina levels.

Main Dose: About 250-500 mg of CTB per day over a period of about 3 to 4 months.

Optional maintenance dose: About 125-250 mg CTB per day over an extended period or indefinitely.

2.2 For subjects undertaking heavy physical activity such as sports persons and desiring increase in BMR, energy, endurance and stamina levels:

Main Dose: About 500-1000 mg CTB per day for a period of about 3 to 4 months.

Optional maintenance dose: About 250-500 mg CTB per day for an extended period or indefinitely.

2.3 An alternative treatment for subjects desiring moderate increased BMR, stamina, energy and endurance levels:

Main Dose: About 90-150 mg, of CTB containing about 2 mg, to 15 mg of saponin glycoside of *caralluma* together with about 100-200 mg of Green tea catechins per day.

Optional maintenance dose: The same as the main dose. Period: extended to indefinite.

2.4 A yet another course of treatment for subjects desiring increase in BMR, energy, endurance and stamina:

Main Dose: About 100-200 mg of CTB containing about 2 mg to 15 mg of saponin glycoside of *caralluma* together with about 100-200 mg of the catechins of green tea and about 100-200 mg of the withanolides of Ashwagandha per day.

Period: About 6-9 months.

Optional Maintenance dose: The same as the main dose Period: extended to indefinite.

At the end of week two, the feeling of fatigue during exercise and workouts comes down and the subject will feel more energetic and capable of more exercise. At week four, male subjects on exercise programs such as weight training will notice an upward trend in bicep circumference, chest circumference and increase in muscle sizes. Female subjects on weight training will see clear signs of loss of fat surrounding muscle groups. The treatment is suitable for housewives whose energy levels tend to sag after the morning round of work.

3. Lean Body Mass:

3.1 For subjects undertaking moderate physical activity and desiring increase in lean body mass:

Main Dose: About 250-500 mg CTB per day over a period of about 3 to 4 months followed by an optional maintenance dose of about 125-250 mg CTB per day over an extended period or indefinitely.

3.2 For subjects undertaking heavy physical activity and desiring increase in lean body mass the main dose provided by the invention is about 500-1000 mg of CTB per day over a period of 3 to 4 months followed by an optional maintenance dose of about 250-500 mg CTB per day over an extended period or indefinitely.

4. Osteo-Arthritis:

4.1 For subjects having early to middle stage osteo-arthritis of weight-bearing joints with mild to moderate radiological symptomatology and desiring relief from joint pains and inflammation: Main Dose: About 250-500 mg CTB per day over a period of about 4 to 5 months followed by an optional maintenance dose of about 125-250 mg CTB per day over an extended period or indefinitely.

4.2 For subjects suffering from severe osteo-arthritis of weight-bearing joints with mild to moderate radiological symptomatology and desiring relief from joint pains and inflammation:

Main Dose: About 500-1000 mg CTB per day over a period of about 4 to 5 months followed by an optional maintenance dose of about 250-500 mg CTB per day over an extended period or indefinitely.

Six alternative courses of treatment for subjects suffering from osteo-arthritis and/or desiring rejuvenation of the weight bearing joints and/or relief from joint pains are provided hereinbelow.

4.3 Main Dose: about 120-300 mg CTB together with about 400-1000 mg of Glucosamine sulphate per day for a period of about 6 to 8 months followed by an optional maintenance dose, the same as the main dose, for a period of about 6 months or indefinitely.

4.4 Main Dose: About 90-270 mg of CTB together with about 250-750 mg of Glucosamine sulphate and about 75 to 250 mg of Rutin per day over a period of about 6 to 8 months followed by an optional maintenance dose, the same as the main dose, for an extended period or indefinitely.

4.5 Main Dose: About 120-300 mg CTB together with about 300 to 900 mg Rutin per day over a period of about 6 to 8 months followed by an optional maintenance dose, the same as the main dose, over an extended period or indefinitely. The maintenance dose may be adopted when the arthritic condition comes under control and the same may be taken in two parts, one morning and one evening.

4.6 Main Dose: About 100-200 mg CTB together with about 600-750 mg glucosamine sulphate per day to be taken in two parts. This dose is provided by the invention as a dietary supplement for subjects over forty years of age and desiring to prevent the onset of osteo-arthritis by the joints going into a degenerative process. This dose ensures adequate synovial fluid secretion and rejuvenates the ligaments. In the hereinmentioned doses the bioflavonoid Rutin may be substituted by one of the other bioflavonoids. And the glucosamine sulphate may be either the sodium or potassium salt. The doses that exclude glucosamine sulphate are advised for subjects that have a gastric acidity problem as glucosamine sulphate has an acidic reaction in the stomach. Period: Over an extended period or indefinitely.

4.7 Main dose: About 120-300 mg of CTB together with about 300-900 mg Rutin and 50-100 mg of bamboo silica (70%) per day over a period of about six to eight months followed by an optional maintenance dose, the same as the main dose, to be taken over an extended period or indefinitely. The main dose may be stopped and the maintenance dose adopted as soon as the arthritic condition is under control.

4.8 Main dose: About 90-270 mg of CTB together with about 250-750 mg of Glucosamine sulphate, 75-250 mg of Rutin and about 50-100 mg of Bamboo silica per day over a period of about six to eight months followed by an optional maintenance dose, the same as the main dose, for a period of about six months or indefinitely.

The pregnane glycosides in the abovementioned doses for osteo-arthritis provide the anti-inflammatory action. This is important as both glucosamine sulphate and chondroitin do not possess anti-inflammation property. The subjects may be on NTHE therapy and/or physiotherapy treatment. *Caralluma* extracts are well-tolerated and exhibit no side effects on prolonged consumption. Preferably the doses may be taken after the meals.

At week three gradual alleviation of pain occurs together with an increase in joint mobility and increased tolerance to physical stress. At week five, the subjects experienced near-normalcy in joint movements and cessation of pain, significant reduction in morning stiffness, increased tolerance to exercise and quicker recovery from exercise. At week 13, further bone degradation ceases almost totally as evidenced by radiological investigations.

Where combination main doses have been provided, the same may be discontinued when the arthritic condition comes under control. From that point, a maintenance dose of about 250 mg of CTB per day may be adopted for a period of six to eight months. The maintenance dose may be preferably taken in two stages after the two main meals of the day. For severe cases, the combination doses may preferably be continued indefinitely.

5. Blood Sugar:

5.1 The treatment provided by this invention for subjects having Type 2 diabetes and FBS(Fasting Blood Sugar) of about 120-150 mg/dL Main Dose: About 500-1000 mg CTB per day Period: prolonged to indefinite 5.2 For subjects having Type 2 diabetes and FBS exceeding about 150 mg/dL Main Dose: About 1000-1500 mg CTB per day over a prolonged period or indefinitely.

The following two alternative courses of treatment are provided by the invention.

5.3 For subjects having Type 2 diabetes and/or desiring control/regulation of blood sugar:

Main Dose: About 100-250 mg CTB together with about 100-200 mg of 4-hydroxy-iso-leucine(or as Fenugreek extract) per day, the pregnane glycoside containing about 2-3% bitters of the *caralluma* species of plants. Period: 6 to 8 months. Optional maintenance dose: the same as the main dose. Period: over an extended period or indefinitely.

5.4 For subjects having Type 2 diabetes.

Main Dose: About 100-200 mg of CTB together with about 100-200 mg of Coccinia extract containing about 10% terpenes, about 100-200 mg of Bitter gourd extract containing about 8% bitters, about 100-200 mg of Cinnamon extract containing about 15% polyphenols and about 100-200 mg. Fenugreek extract containing about 40% 4-hydroxy-iso-leucine per day for a period of about 6-7 months followed by an optional maintenance dose, the same as the main dose, preferably for an indefinite period.

Preferably the doses are taken 30 min. after meals. The dose may be taken in one stage or in two. At week two the subject would experience a reduction of about 10% in FBS and PPBS(Post-prandial blood sugar). At week four onwards, weight loss will be observed and also increased physical stamina. Blood sugar levels further. About 20% reduction in FBS and PPBS can be expected at this period. At week 16, reduction in glycosylated hemoglobin will be observed. Subjects may stop their main dose after the stipulated period for a period of about 6-8 months. They may then revive the main dose for about 2-3 months after a gap of about 2-3 months. This sequence may be continued indefinitely. For subjects over forty years of age, it is preferable that the sequence is continued indefinitely. For subjects over fifty, preferably the main dose should be continued indefinitely. Regular exercise in the form of a brisk walk of 45 minute morning and evening is advised and it is suggested that subjects avoid refined carbohydrate foods.

6. Blood Pressure:

6.1 For subjects suffering from mild to moderate hypertension the main dose provided by the invention comprises about 250-500 mg of CTB per day to be taken over a period of about 3 to 4 months followed by an optional maintenance dose of about 125-250 mg of CTB per day for an extended period or indefinitely.

6.2 For subjects having severe hypertension the treatment provided by the invention comprises: Main Dose: About 500-1000 mg of CTB per day for a period of about 3 to 4 months followed by a maintenance dose of about 250-500 mg of CTB per day for an extended period or indefinitely.

6.3 An alternative course is provided by the invention for subjects having mild to moderate hypertension wherein the main dose is about 125-250 mg of CTB together with about 125-250 mg of HCA(*Garcinia* extract) per day to be taken over an indefinite period.

6.4 A still another alternative course of treatment and management for this condition comprises a main dose of about 125-250 mg of CTB together with about 125-250 mg of Commiphora Mukul extract containing about 3% gugulsterones per day to be taken over an indefinite period.

The tests have established that pregnane glycoside(s) reduce blood pressure, both systolic and diastolic. Another related effect is that of reducing serum LDL(Low density lipoprotein) and enhancing the HDL(High density lipoprotein). The dose may be taken in one stage or two and is preferably taken after meals. At week three, the effects observed: increased energy and exercise endurance. This brings down the LDL levels. Physical training is advised during the treatment. At week five, increase in the HDL level and further increases in energy and endurance are observed.

7. Appetite Reduction:

7.1 For subjects desiring mild to moderate reduction in appetite, this invention provides: Main Dose: about 250-500 mg of CTB per day over a prolonged period or indefinitely.

7.2 For subjects desiring heavy reduction in appetite: Main Dose: about 500-1000 mg of CTB per day over a prolonged period or indefinitely.

7.3 This invention provides an alternative course comprising pregnane glycosides and HCA. Main dose: About 120-240 mg of CTB with 150-300 mg of HCA per day over a period of about six months. Optional Maintenance dose: the same as the main dose. Period: extended period to indefinitely.

*Garcinia* extract may be used in place of HCA.

8. Weight Reduction:

8.1 For subjects desiring slow/gradual reduction in weight: Main Dose: about 250-500 mg of CTB per day over a period of about 3 to 4 months followed by an optional maintenance dose of about 125-250 mg CTB per day taken over an extended period or indefinitely.

8.2 For subjects desiring rapid reduction in weight: Main Dose: about 500-1000 mg CTB per day over a period of about 3 to 4 months followed by an optional maintenance dose of about 250-500 mg CTB per day over an extended period or indefinitely.

8.3 This invention provides an alternative course comprising pregnane glycosides and HCA. Main dose: About 120-240 mg of CTB with 150-300 mg of HCA per day over a period of about six months. Optional Maintenance dose: the same as the main dose. Period: extended period to indefinitely.

*Garcinia* extract may be used in place of HCA.

9. Waist, Arm and Hip Circumference:

9.1 For subjects desiring reduction in waist, hip and arm circumferences: Main Dose: About 250-500 mg of CTB per day over a period of about 3 to 4 months followed by an optional maintenance dose of about 125-250 mg CTB per day over an extended period or indefinitely.

9.2 This invention provides an alternative course comprising pregnane glycosides and HCA. Main dose: About 120-240 mg of CTB with 150-300 mg of HCA per day over a period of about six months. Optional Maintenance dose: same as the main dose. Period: extended period to indefinitely.

*Garcinia* extract may be used in place of HCA.

10. Migraine:

For a subject desiring relief from migraine: Main Dose: about 500-1000 mg of CTB per day over a period of about 3 to 4 months, the dose to be doubled during the periods of attack.

The daily dose may be preferably taken in two parts one after each meal. At week five, the subject will notice decreased frequency of attacks. The pregnane glycosides exert their anti-inflammatory properties and also restore elasticity to the capillaries. The anti-depressant property of pregnane glycosides gives a psychological boost to the subject. His confidence level increases due to increased secretion of serotonin.

At week nine, the subject experiences significantly reduced frequency of attacks and increased tolerance to physical stress. At week thirteen, the frequency of attacks would be down to less than 10%. A maintenance dose of about 125-250 mg of CTB per day may preferably be continued indefinitely.

11. Clinical Depression:

11.1 For a subject suffering from mild clinical depression: Main Dose: about 125-250 mg of CTB per day to be taken till the ceasing of the symptoms.

11.2 For subjects suffering from severe clinical depression: Main Dose: about 250 to 1000 mg CTB per day to be taken till the ceasing of the symptoms.

11.3 An alternative course provided by the invention for a subject suffering from clinical depression or desiring mood elevation comprises a main dose of about 250-500 mg CTB per day together with about 100-200 mg of the withanolides of Ashwagandha over a period of about 12 to 18 months followed by an optional maintenance dose of about 125-250 mg of CTB per day together with about 50-100 mg of the withanolides of Ashwagandha over an extended period or indefinitely.

Depressions are associated with abnormal levels of serotonin reuptake. Pregnane glycosides cause increase in serotonin levels without the adverse effects such as serotonin intoxication of known anti-depressants such as the SSRI's. With pregnane glycosides, subjects experience increased feeling of well-being, increased energy levels, increase tolerance to stress and a general improvement in mood inter alia through its effect on serotonin levels. Adverse effects, if any, are of a milder form than with the SSRI's. The subjects begin to experience increased energy levels, reduced fatigue and tiredness and general well-being at week three. At week four, there is further all-round in the abovementioned parameters and the subjects experience increased social interests.

12. Sexual Dysfunction:

12.1 For a subject suffering from primary impotence and/or decreased libido and/or desiring increased libido and sexual drive, power and stamina: Main Dose: About 500-1000 mg of CTB per day over the period of existence of dysfunction and decreased libido or as desired by the subject.

12.2 An alternative course provided by the invention for a subject suffering from a sexual dysfunction such as primary impotency and/or reduced libido or desiring increased sex drive, power and stamina: Main Dose: About 250-500 mg of CTB per day together with about 100-200 mg of the withanolides of Ashwagandha over a period of about 6 to 12 months followed by an optional maintenance dose of about 125-250 mg of CTB per day together with about 50-100 mg of the withanolides of Ashwagandha as long as necessary or as long as increase in sex power is desired.

12.3 A yet another alternative course provided by the invention for a subject suffering from a sexual dysfunction such as primary impotence and/or loss of, or reduced libido and/or desiring increased sex power, stamina and drive:

Main Dose: About 250-500 mg of CTB per day together with about 100-200 mg of Shilajith over a period of about 6 to 12 months followed by an optional maintenance dose of about 125-250 mg CTB per day together with about 50-100 mg of Shilajith for as long as necessary or as long as increased sex drive is desired.

12.4 A yet another course of treatment provided by the invention for a subject suffering from a sexual dysfunction such as primary impotence and/or loss of, or reduced libido and/or desiring increased sex power/drive and stamina. Main dose: About 250-500 mg of CTB per day together with about 250-500 mg of Fenugreek extract containing about 50% Protodioscin to be taken over a period of about 3-4 months followed by an optional maintenance dose of about 125-250 mg of CTB together with about 125-250 mg of the fenugreek extract per day for as long as necessary or as long as increased sex drive is desired.

The effects of pregnane glycosides relevant to its application in treatment of a sexual dysfunction are: increase in energy, endurance and stamina, beneficial effect on capillaries, feeling of increased well-being, increased tolerance to stress, elevation of the mood and others. Together these effects appear to produce increased blood flow in the region of the reproductive organs and cause resurgence of sexual interest and increase of libido which has been clearly established by the tests/trials. *Caralluma* extracts also appear to be beneficial for women in the post-menopausal phase when they experience reduced sexual desire, painful intercourse, diminished sexual responsiveness, difficulty in achieving orgasm and decreased genital sensation. Pregnane glycosides do not have the cardiovascular and other side effects exhibited by the known compounds for treatment of a sexual dysfunction, such as, for example, the PDE5 inhibitors.

13. Cognitive and Memory Function:

For a subject suffering from diminished cognitive and memory function or desiring increase thereof: Main Dose: about 250-500 mg of CTB per day over a period of about 3 to 4 months.

*Caralluma* extracts have a beneficial effect on neurotransmitter levels and functioning and, in particular, on serotonin levels. It appears that the multiple effects of pregnane glycosides on a subject have a cascade type effect causing an all-round improvement in body functions including cognitive and memory function including memory recall and retention and speed of retrieval. This has been established by the tests/trials. The dose may be taken in a single stage or two and is preferably taken after meals.

14. Aging Syndrome:

14.1 For subjects desiring treatment/management of the aging syndrome, this invention provides for a main dose of about 250-500 mg of CTB per day over a prolonged to indefinite period.

14.2 An alternative course provided by the invention comprises a dose of about 100-200 mg of CTB per day together with about 100-200 mg of the catechins of green tea and about 100-200 mg of the saponin glycoside of *caralluma* followed by an optional maintenance dose of about 100-200 mg of CTB per day together with about 50-100 mg of the catechins and about 120-300 mg of the saponin glycoside over an indefinite period.

14.3 This invention also provides a dietary supplement for fighting the aging syndrome comprising a dose of about 100-200 mg of CTB per day together with about 250 to 350 mg of Green Tea extract containing about 40% catechins to be taken indefinitely.

14.4 A yet another composition provided by this invention for a subject desiring reduction in the aging syndrome comprises a main dose of about 50-100 mg of CTB per day together with about 100-150 mg of zinc monomethionine, about 150-250 mg of citrus bioflavonoids and selenium chelate equivalent to about 2-8 mg of selenium to be taken over an indefinite period.

The properties of pregnane glycosides relevant to its application as an anti-oxidant and in combating aging are: (i) Reduction of fat; (ii) Increase of energy levels and stamina levels, (iii) Increased physical activity; (iv) lowered stress and mood elevation; (v) increased joint mobility; (vi) increasing capillary elasticity and others. These benefits are obtained with substantially nil side effects.

15. Loss of Hearing:

15.1 For a subject suffering from hearing loss: Main Dose: About 250-500 mg of CTB per day over a period of about 3 to 4 months followed by an optional maintenance dose of about 125-250 mg of CTB per day taken over an extended period or indefinitely.

16. Circulation Disorder:

16.1 For a subject suffering from a circulation disorder: Main Dose: about 500-1000 mg of CTB per day over a period of about 3 to 4 months followed by an optional maintenance dose of about 250-500 mg per day of CTB over an indefinite period. The invention provides for the maintenance dose to be taken indefinitely in case of severe circulation disorder and where the disorder is mild and the maintenance dose is not adopted then the main dose should be commenced upon re-occurrence of the disorder/symptom. The main dose must be revived if the circulation problem re-occurs and in cases of severe circulation problems the main dose should preferably be continued indefinitely.

17. Capillary Degeneration:

17.1 For a subject desiring restoration or maintenance of capillary elasticity: Main Dose: About 500-1000 mg of CTB per day for a period of about 3 to 4 months followed by a maintenance dose of about 250-500 mg of CTB per day to be taken over an indefinite period.

It has been observed that *caralluma* extracts enhance/restore capillary elasticity. Together with the other effects of pregnane glycosides, the subject experiences an all-round improvement of body functions including hearing, sexual function, skin health, mental functions, circulation and others. The dosage may be taken in one stage or two and is preferably taken in two stages after the two main meals of the day.

18. Skin Nourishment:

For a subject desiring skin nourishment and skin elasticity and health: Main Dose: About 50-100 mg of CTB per day together with about 100-150 mg of zinc monomethionine, about 150-250 mg of citrus bioflavonoids and about 2 to 8 mg of selenium as selenium chelate or other compound, to be taken over an extended period or indefinitely.

19. Menopausal Syndrome:

19.1 For a subject suffering from the menopausal syndrome and desiring alleviation from hot flushes and menopausal distress: Main Dose: About 50-100 mg of CTB per day together with about 100-150 mg of zinc monomethionine, about 150-200 mg of Citrus bioflavonoids and about 6-10 mg of selenium as selenium chelate or other compound to be taken as long as necessary.

Four further courses of treatment and management for a subject suffering from menopausal syndrome are indicated hereinbelow.

19.2 Main dose: About 50-100 mg of CTB together with about 100-200 mg Liquorice extract containing about 5% Triphytoestrogens per day to be taken as long as necessary and as long as symptoms last.

19.3 Main dose: About 50-100 mg of CTB together with about 100-200 mg of Red clover extract containing about 8% isoflavones per day to be taken for as long as necessary and as long as symptoms last.

19.4 Main Dose: About 50-100 mg of CTB together with about 100-200 mg of Hops flower extract containing about 5% triphytoestrogens per day to be taken for as long as necessary and as long as symptoms last.

19.5 Main dose: About 50-100 mg of CTB together with about 100-200 mg of Pomegranate extract containing about 10% Ellagic acid per day. Period: As long as the symptoms and as long as necessary.

20. Cancer Prevention/Protection:

20.1 For a subject desiring the neutralization of carcinogens and protection against cancer: Main Dose: About 50-100 mg of CTB per day together with about 100-150 mg of zinc monomethionine, about 150-200 mg of citrus bioflavonoids and about 2-8 mg of selenium as selenium chelate or other compound to be taken indefinitely.

21. Cholesterol:

21.1 For a subject desiring reduction of total blood cholesterol: Main Dose: About 125-500 mg of CTB per day together with about 150-250 mg of *Hibiscus Subdariffa* extract containing about 25% polyphenols and about 100-200 mg of Commiphora Mukul extract containing about 3% gugulsterones to be taken for an indefinite period.

21.2 An alternative composition provided by the invention for a subject desiring reduction in blood cholesterol: Main Dose: About 120-240 mg of CTB per day together with about 150-300 mg of HCA over a period of about six months followed by an optional maintenance dose, the same as the main dose over an extended period or indefinitely preferably over an indefinite period.

21.3 A yet another alternative composition provided by the invention for a subject desiring reduction in blood cholesterol: Main Dose: About 90-150 mg of CTB containing about 2-10% saponin glycoside, together with about 100-200 mg of the catechins of green tea per day over an extended period or indefinitely.

22. BMI:

For a subject desirous of reducing BMI, the invention provides for the following courses of treatment and management.

22.1 For subjects of either gender having a BMI of about 25 to 30, Type 2 diabetes or normal, normotensive or mild to moderate hypertension with no systemic dysfunction, the subject being preferably on controlled diet and/or moderate physical activity, otherwise no restriction.

Main Dose: About 250-500 mg of caratuberside(CTB) per day over a period of 3 to 4 months followed by an optional maintenance dose of about 125-250 mg CTB per day for about six to eight months. The maintenance dose may be taken over an extended period or indefinitely without any adverse effects as *caralluma* pregnane glycosides are good anti-oxidants, nontoxic and well-tolerated nutritional supplements.

22.2 For subjects of either gender having a BMI of about 30 to 50, Type 2 diabetes or normal, normotensive or mild to moderate hypertension with no systemic dysfunction, the subject being preferably on controlled diet and/or moderate physical activity, otherwise no restriction, a treatment dose double that provided above for the lower BMI category of subjects and optional maintenance dosage, the same as for the lower BMI category, is provided, all other parameters including the period for the doses being the same as for the lower BMI category.

22.3 An alternative schedule for the maintenance dose is to take the same for a period of about 4-5 months and then stop the same for a period of about 6 months. The maintenance dose may be again started at the end of the 6 month period and continued for about three months. The maintenance course may be continued under this sequence of six and three months for an indefinite period. The water intake should be double of the normal during the treatment. During the treatment one-half hour brisk walks morning and evening and diet control are advised.

By about the fifth week, subjects start feeling the lessening of appetite and of the thoughts of food and simultaneously feel more energetic. Appetite is experienced by the subjects at appropriate times but is satisfied with lesser amounts of food. From this point onwards, lowering of the BMI(weight loss) also begins to become quite apparent.

22.4 Main dose: About 120-240 mg of CTB with 150-300 mg of HCA per day over a period of about six months. Optional Maintenance dose: the same as the main dose. Period: extended period to indefinitely.

*Garcinia* extract may be used in place of HCA.

23. Anti-Oxidation:

23.1 This invention provides for an anti-oxidation course for subjects desiring treatment/management of the aging syndrome and/or for general fitness and health, this invention provides for a main dose of about 250-500 mg of CTB per day over a prolonged to indefinite period.

23.2 An alternative anti-oxidation course provided by the invention comprises a dose of about 100-200 mg of CTB per day together with about 100-200 mg of the catechins of green tea and about 100-200 mg of the saponin glycoside of *caralluma* followed by an optional maintenance dose of about 100-200 mg of CTB per day together with about 50-100 mg of the catechins and about 120-300 mg of the saponin glycoside over an indefinite period.

23.3 This invention also provides an anti-oxidant dietary supplement for fighting the aging syndrome and/or provide general health and fitness comprising a dose of about 100-200 mg of CTB per day together with about 250 to 350 mg of Green Tea extract containing about 40% catechins to be taken indefinitely.

23.4 A yet another composition course provided by this invention for a subject desiring reduction in the aging syndrome and/or ensuring general health and fitness comprises a main dose of about 50-100 mg of CTB per day together with about 100-150 mg of zinc monomethionine, about 150-250 mg of Citrus bioflavonoids and selenium chelate equivalent to about 2-8 mg of selenium to be taken over an indefinite period.

The properties of pregnane glycosides relevant to its application as an anti-oxidant and in combating aging are: (i) Reduction of fat; (ii) Increase of energy levels and stamina levels; (iii) Increased physical activity; (iv) lowered stress and mood elevation; and (v) increased joint mobility. These benefits are obtained with substantially nil side effects.

In all the treatments described hereinabove, the dosages may be taken before, during or after meals. However, where the objective is to provide relief from one or more of the obesity-related symptoms the dosages may be preferably taken one-half to one hour before meals. A daily dose may be taken at one time or in two stages. If taken at one time, it may be preferably taken before, during or after the main meal of the day.

The term 'indefinitely' used in relation to the treatment and maintenance doses is intended to mean that the doses are to be taken lifelong. The scope of the term 'indefinitely' is intended to include the possibility of taking the dose in a sequential arrangement comprising taking the doses periodically over periods of about two to six months with the gaps also extending to about two to six months. In the applications related to obesity-related symptoms, the sequential formula for maintenance doses described hereinabove is recommended. Various embodiments and variations other than described hereinabove that are within the art are within the scope of the invention.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A composition for a medicinal or health effect, comprising: a concentrated pregnane glycoside-containing *Caralluma* extract produced by a process comprising providing a *Caralluma* plant material, extracting the *Caralluma* plant material by using a first solvent to obtain a solution, concentrating the solution to obtain the concentrated pregnane glycoside-containing *Caralluma* extract, and further comprising: substantially removing resinous material before the extracting, during the extracting, after the extracting, before the concentrating, or during the concentrating, whereby the resinous material does not exceed 1% w/w of concentrated *Caralluma* extract; and at least one second component selected from the group consisting of a fenugreek extract having 4-hydroxy-isoleucine obtained from fenugreek by a process including a chemical extraction; hydroxyl-isoleucine; protodioscine; zinc monomethionine; glucosamine; glucosamine with rutin; rutin; chondroitin; bioflavonoid; selenium; a *Garcinia* extract; hydroxycitrate; a green tea extract; saponin glycoside; an ashwagandha extract; a shilajith; a *Coccinia* extract containing terpenes; a bitter gourd extract containing bitters; a *Hibiscus subdariffa* extract containing polyphenols; a cinnamon extract containing polyphenols; a *Commiphora mukul* extract containing gugulsterones; a liquorice extract containing tripytoestrogen; a red clover extract containing isoflavones; a flower extract of hops containing triphyotestrogen; a pomegranate extract containing ellagic acid; and bamboo silica.

2. The composition of claim 1, wherein the pregnane glycoside comprises caratuberside and bouceroside.

3. The composition of claim 2, wherein a ratio of caratuberside to bouceroside is from 9:1 to 11:1.

4. The composition of claim 1, wherein the *Caralluma* extract comprises about 25% to 50% by wt of the pregnane glycosides.

5. The composition of claim 4, wherein the pregnane glycoside comprises caratuberside and bouceroside.

6. The composition of claim 5, wherein a ratio of the caratuberside to the bouceroside is from 9:1 to 11:1.

7. The composition of claim 1, wherein the pregnane glycoside is in the form of pharmaceutically acceptable salt.

8. The composition of claim 1, further comprising a pharmaceutically acceptable carrier.

9. The composition of claim 1, wherein the *Caralluma* extract further comprises a bitter.

10. The composition of claim 1, wherein the second component is hydroxycitrate.

11. The composition of claim 1, wherein the second component is glucosamine.

12. The composition of claim 1, wherein the second component is glucosamine and rutin.

13. The composition of claim 1, wherein the second component is glucosamine, rutin, and chondroitin.

14. The composition of claim 1, wherein the second component is 4-hydroxy-isoleucine.

15. The composition of claim 1, wherein the second component comprises the fenugreek extract containing 4-hydroxy-iso-leucine, the *Coccinia* extract containing about 10% terpenes, the bitter gourd extract containing about 8% bitters, and the cinnamon extract containing about 15% polyphenols.

16. The composition of claim 1, wherein the second component comprises about 50% w/w protodioscin.

17. The composition of claim 1, wherein the second component comprises the zinc monomethionine, and bioflavonoids with selenium.

18. The composition of claim 1, wherein the second component comprises rutin and bamboo silica.

19. The composition of claim 1, wherein the second component comprises glucosamine, rutin and bamboo silica.

20. The composition of claim 1, wherein the second component is saponin glycoside.

21. A composition for a medicinal or health effect, comprising: a first component comprising a pregnane glycoside-containing *Caralluma* extract produced by a process comprising providing a *Caralluma* plant material, extracting the *Caralluma* plant material by using a first solvent to obtain a solution, substantially removing resinous material from the solution, and concentrating the solution to obtain the pregnane glycoside-containing *Caralluma* extract, whereby the extract comprises resinous material of equal to or less than about 0.5% w/w of said *Caralluma* extract; and at least one second component selected from the group consisting of a fenugreek extract having 4-hydroxy-isoleucine obtained from fenugreek by a process including a chemical extraction; hydroxyl-isoleucine; protodioscine; zinc monomethionine; glucosamine; glucosamine with rutin; rutin; chondroitin; bioflavonoid; selenium; a *Garcinia* extract; hydroxycitrate; a green tea extract; saponin glycoside; an ashwagandha extract; a shilajith; a *Coccinia* extract containing terpenes; a bitter gourd extract containing bitters; a *Hibiscus subdariffa* extract containing polyphenols; a cinnamon extract containing polyphenols; a *Commiphora mukul* extract containing gugulsterones; a liquorice extract containing tripytoestrogen; a red clover extract containing isoflavones; a flower extract of hops containing triphyotestrogen; a pomegranate extract containing ellagic acid; and bamboo silica.

22. The composition of claim 21, wherein the pregnane glycoside comprises caratuberside and bouceroside.

23. The composition of claim 21, wherein the *Caralluma* extract comprises about 25% to 50% by wt of the pregnane glycosides.

24. The composition of claim 21, wherein the pregnane glycoside is in the form of pharmaceutically acceptable salt.

25. The composition of claim 21, further comprising a pharmaceutically acceptable carrier.

26. The composition of claim 21, wherein the Caralluma extract further comprises a bitter.

27. The composition of claim 21, wherein the second component is hydroxycitrate.

28. The composition of claim 21, wherein the second component is glucosamine.

29. The composition of claim 21, wherein the second component is glucosamine and rutin.

30. The composition of claim 21, wherein the second component is glucosamine, rutin, and chondroitin.

31. The composition of claim 21, wherein the second component is 4-hydroxy-isoleucine.

32. The composition of claim 21, wherein the second component comprises the fenugreek extract containing 4-hydroxy-iso-leucine, the *coccinia* extract containing about 10% terpenes, the bitter gourd extract containing about 8% bitters, and the cinnamon extract containing about 15% polyphenols.

33. The composition of claim 21, wherein the second component comprises about 50% w/w protodioscin.

34. The composition of claim 21, wherein the second component comprises the zinc monomethionine, and bioflavonoids with selenium.

35. The composition of claim 21, wherein the second component comprises rutin and bamboo silica.

36. The composition of claim 21, wherein the second component comprises glucosamine, rutin and bamboo silica.

37. The composition of claim 1, wherein the second component is saponin glycoside.

38. The composition of claim 22, wherein a ratio of the caratuberside to the bouceroside is from 9:1 to 11:1.

39. The composition of claim 1, wherein an amount of the *Caralluma* extract is 250 mg, and an amount of the fenugreek extract is 250 mg.

40. The composition of claim 21, wherein an amount of the pregnane glycoside is 125 mg, and an amount of the fenugreek extract is 250 mg.

* * * * *